(12) United States Patent
Wang

(10) Patent No.: US 9,025,017 B2
(45) Date of Patent: May 5, 2015

(54) DETECTION OF WHEN A CAPSULE CAMERA ENTERS INTO OR GOES OUT OF A HUMAN BODY AND ASSOCIATED OPERATIONS

(75) Inventor: Kang-Huai Wang, Saratoga, CA (US)

(73) Assignee: Capso Vision, Inc., Saratoga, CA (US)

( * ) Notice: Subject to any disclaimer, the term of this patent is extended or adjusted under 35 U.S.C. 154(b) by 711 days.

(21) Appl. No.: 13/372,101

(22) Filed: Feb. 13, 2012

(65) Prior Publication Data

US 2012/0169859 A1    Jul. 5, 2012

Related U.S. Application Data

(62) Division of application No. 11/625,647, filed on Jan. 22, 2007, now Pat. No. 8,187,174.

(51) Int. Cl.
*H04N 7/18* (2006.01)
*A61B 1/04* (2006.01)
*A61B 5/06* (2006.01)
*A61B 5/00* (2006.01)

(52) U.S. Cl.
CPC . *A61B 1/041* (2013.01); *A61B 5/06* (2013.01); *A61B 5/42* (2013.01)

(58) Field of Classification Search
CPC ............ A61B 1/041; A61B 5/06; A61B 5/42; A61B 1/05; A61B 1/042; H04N 2005/2255; H04N 5/2354; H04N 5/2256
USPC .......................................................... 348/68
See application file for complete search history.

(56) References Cited

U.S. PATENT DOCUMENTS

| 4,485,315 | A | | 11/1984 | Collet et al. |
| 5,604,531 | A | * | 2/1997 | Iddan et al. .................... 348/76 |
| 6,664,909 | B1 | * | 12/2003 | Hyde et al. ................... 341/144 |
| 7,495,993 | B2 | * | 2/2009 | Wang ...................... 365/230.09 |
| 7,796,870 | B2 | * | 9/2010 | Wang .............................. 396/14 |
| 8,102,007 | B1 | * | 1/2012 | Hyde et al. .................... 257/371 |
| 8,187,174 | B2 | * | 5/2012 | Wang ............................ 600/117 |
| 8,500,630 | B2 | * | 8/2013 | Gilad et al. ................... 600/160 |
| 2001/0035902 | A1 | * | 11/2001 | Iddan et al. .................... 348/76 |
| 2002/0158976 | A1 | | 10/2002 | Vni et al. |

(Continued)

FOREIGN PATENT DOCUMENTS

WO    2004/082472    9/2004

OTHER PUBLICATIONS

ASGE, Technology Status Evaluation Report, Wireless capsule endoscopy, vol. 78, No. 6, 2013.*

(Continued)

*Primary Examiner* — Andy Rao
*Assistant Examiner* — Shan Elahi
(74) *Attorney, Agent, or Firm* — Edward C. Kwok; Hogan Lovells US LLP

(57) ABSTRACT

A method for detecting a capsule camera entering into or exiting the GI tract, includes (a) taking a first test image under the condition that an illumination system of the capsule camera is disabled; (b) taking a second test image under the same condition as the first test image; (c) comparing selected corresponding pixel values of the first test image and the second test image to determine if a significant change in pixel values has occurred; and (d) upon detecting the significant change in pixel values, determining if the capsule camera has entered or exited the GI tract, and performing operations appropriate to follow such determination.

8 Claims, 15 Drawing Sheets

(56) References Cited

U.S. PATENT DOCUMENTS

| | | |
|---|---|---|
| 2003/0020810 A1* | 1/2003 | Takizawa et al. ............... 348/68 |
| 2003/0211405 A1* | 11/2003 | Venkataraman .................. 430/7 |
| 2004/0087832 A1 | 5/2004 | Glukhovsky et al. |
| 2004/0109488 A1* | 6/2004 | Glukhovsky et al. ......... 374/120 |
| 2004/0193029 A1 | 9/2004 | Glukhovsky |
| 2004/0267240 A1* | 12/2004 | Gross et al. ................. 604/890.1 |
| 2005/0043634 A1* | 2/2005 | Yokoi et al. ................... 600/476 |
| 2005/0058701 A1* | 3/2005 | Gross et al. ................... 424/451 |
| 2006/0050145 A1 | 3/2006 | Tanimoto |
| 2006/0229592 A1 | 10/2006 | Yokoi et al. |
| 2006/0285732 A1 | 12/2006 | Horn et al. |
| 2007/0106111 A1 | 5/2007 | Horn et al. |
| 2007/0116119 A1* | 5/2007 | Wang ....................... 375/240.12 |
| 2007/0158776 A1 | 7/2007 | Julio et al. |
| 2007/0249900 A1* | 10/2007 | Wilson et al. ................. 600/116 |
| 2007/0255098 A1* | 11/2007 | Wang et al. ................... 600/109 |
| 2007/0264732 A1* | 11/2007 | Chen ............................... 438/22 |
| 2008/0033247 A1* | 2/2008 | Wilson et al. ................. 600/115 |
| 2008/0045792 A1 | 2/2008 | Shimizu et al. |
| 2008/0117968 A1* | 5/2008 | Wang ....................... 375/240.12 |
| 2008/0143822 A1* | 6/2008 | Wang et al. ..................... 348/36 |
| 2008/0275430 A1* | 11/2008 | Belsky et al. .............. 604/890.1 |
| 2009/0299140 A1* | 12/2009 | Wang ............................. 600/118 |
| 2009/0322865 A1* | 12/2009 | Wang et al. ..................... 348/68 |
| 2011/0060189 A1* | 3/2011 | Belson .......................... 600/117 |

OTHER PUBLICATIONS

Moglia et al, Wireless capsule endoscopy: from diagnostic devices to multipurpose robotic systems, Dec. 12, 2006.*

Moglia et al. "Wireless Capsule Endoscopy: From Diagnostic Devices to Multipurpose Robotic Systems," Biomed Microdevices (2007) v.9: pp. 235-243, Dec. 12, 2006.

Moglia et al. "Recent Patents on Wireless Capsule Endoscopy" Recent Patents on Biomedical Engineering 2008, v.1, pp. 24-33, Nov. 21, 2007.

International Search Report for International Application No. PCT/US2008/050763 dated Jul. 18, 2008, 4 pages.

Written Opinion of the International Searching Authority for International Application No. PCT/US2008/050763 dated Jul. 18, 2008, 11 pages.

* cited by examiner

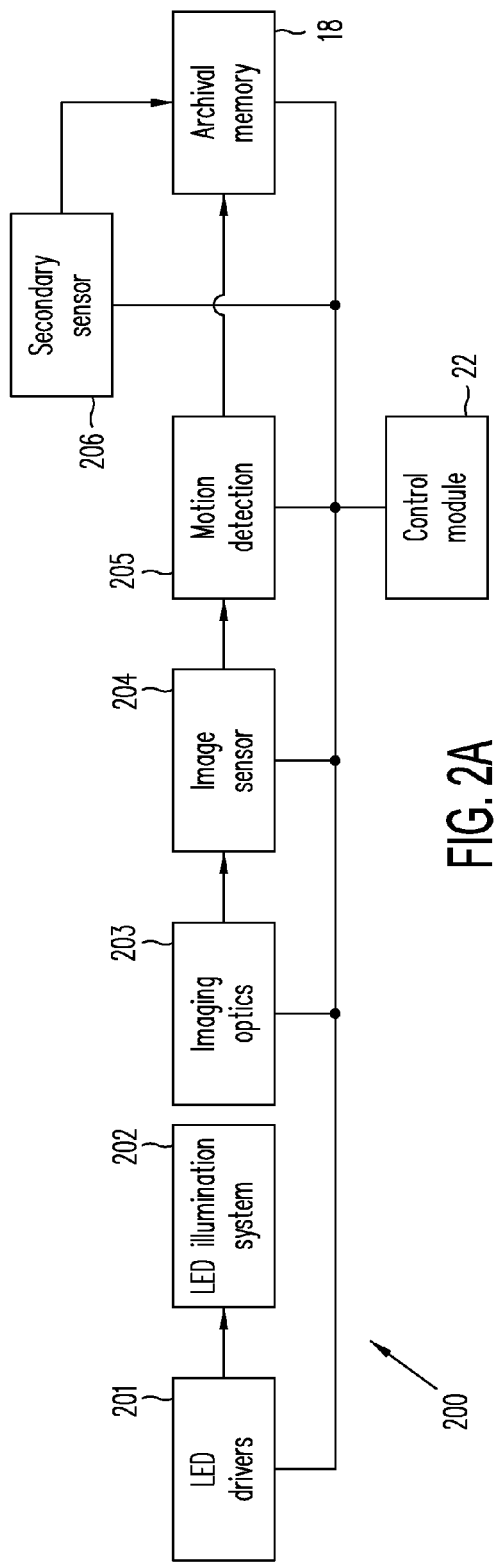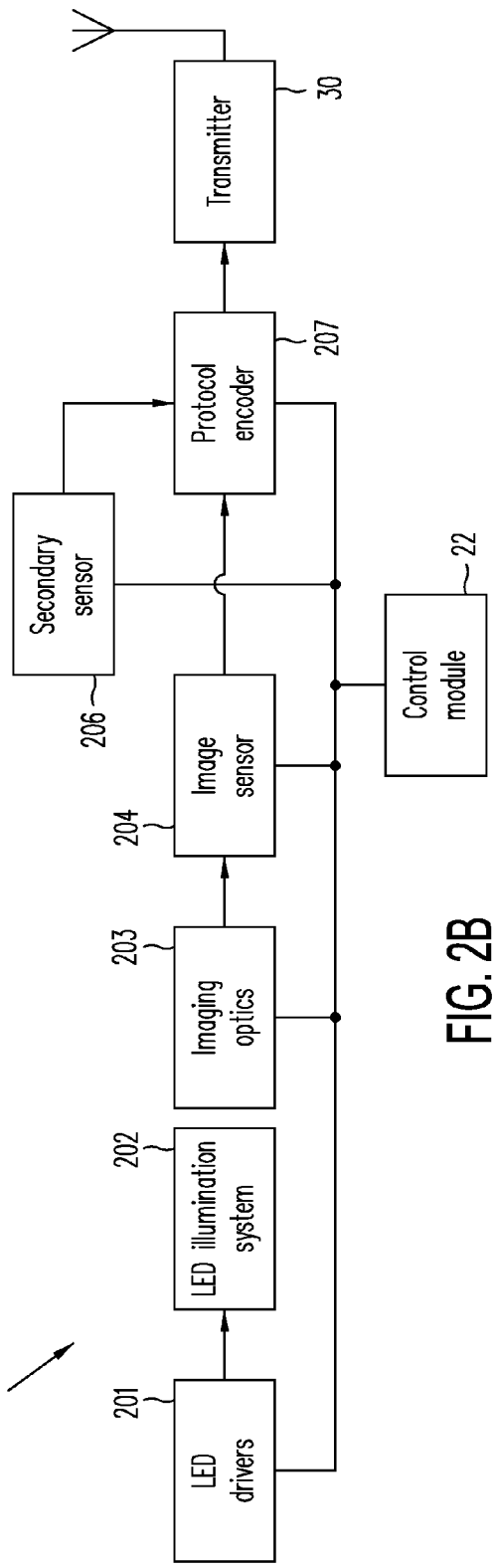
FIG. 2A
FIG. 2B

DETECTION OF WHEN A CAPSULE CAMERA ENTERS INTO OR GOES OUT OF A HUMAN BODY AND ASSOCIATED OPERATIONS

CROSS REFERENCE TO RELATED APPLICATIONS

The present application is a divisional of U.S. patent application Ser. No. 11/625,647 filed Jan. 22, 2007 now U.S. Pat. No. 8,187,174, incorporated herein by reference.

BACKGROUND OF THE INVENTION

1. Field of the Invention

The present invention relates to swallowable capsule cameras. In particular, the present invention relates to methods the capsule camera to detect its own location.

2. Discussion of the Related Art

Devices for imaging body cavities or passages in vivo are known in the art and include endoscopes and autonomous encapsulated cameras. Endoscopes are flexible or rigid tubes that are passed into the body through an orifice or surgical opening, typically into the esophagus via the mouth or into the colon via the rectum. An image is taken at the distal end using a lens and transmitted optically to the proximal end located outside the body, either by a lens-relay system or by a coherent fiber-optic bundle. Alternatively, an instrument may record an image electronically at the distal end (e.g., using a CCD or CMOS array) and transfers the image data electrically to the proximal end through a cable. Endoscopes allow a physician control over the field of view and are well-accepted diagnostic tools. However, they have a number of limitations, present risks to the patient, and are invasive and uncomfortable for the patient. The cost of these procedures restricts their application as routine health-screening tools.

Because of the difficulty traversing a convoluted passage, endoscopes cannot reach the majority of the small intestines and special techniques and precautions—that increase cost—are required to reach the entirety of the colon. Endoscopic risks include the possible perforation of the bodily organs traversed and complications arising from anesthesia. Moreover, a trade-off must be made between patient pain during the procedure and the health risks and post-procedural downtime associated with anesthesia. Therefore, endoscopy is necessarily an in-patient service that involves a significant amount of time from clinicians and thus is a costly procedure.

An alternative in vivo image sensing technique is capsule endoscopy. In capsule endoscopy, a camera is housed in a swallowable capsule, along with a radio transmitter for transmitting data (which consists primarily of images recorded by the camera) to a base-station receiver or transceiver in a data recorder located outside the body. The capsule may also include a radio receiver for receiving instructions or other data from a base-station transmitter. Instead transmitting in a radio frequency, lower frequency electromagnetic signals may be used. Power may be supplied inductively from an external inductor to an internal inductor within the capsule or from a battery within the capsule.

An early example of a camera in a swallowable capsule is described in the U.S. Pat. No. 5,604,531, issued to the Ministry of Defense, State of Israel. A number of patents assigned to Given Imaging describe more details of such a system, using a transmitter to send the camera images to an external receiver. Examples are disclosed in U.S. Pat. Nos. 6,709,387 and 6,428,469. There are also a number of patents to the Olympus Corporation describing a similar technology. For example, U.S. Pat. No. 4,278,077 shows a capsule with a camera for the stomach, which includes film in the camera. U.S. Pat. No. 6,939,292 shows a capsule with a buffering memory, a timer, and a transmitter. U.S. Pat. No. 6,800,060 describes a swallow-able capsule camera that may be retrieved after passing from the body; that capsule camera uses an expensive and rare ultra-high-density atomic-resolution storage (ARS) medium to store images taken.

Introducing the capsule camera into a patient's body begins with removing the capsule from a package having a reed switch. While inside the package, a magnet keeps the reed switch in the capsule in the "off" position. In the "off" position, the capsule camera draws no power. Once removed from the package, the capsule is switched on, as the magnetic force is no longer holding back the metal spring that keeps the reed switch in the "off" position. The patient then swallows the capsule. In the prior art, another approach to activate the capsule camera includes providing a conductive liquid inside the capsule. By shaking the capsule strongly enough in the right direction, the conductive liquid causes contact be made an end of a pipe or chamber, which connects the system to a power source, so as to begin operation.

It is generally not necessary to take pictures when the capsule camera is outside the human body. Storing or transmitting pictures taken outside the body wastes power and takes up valuable space for archiving images. There are a few operations that a capsule camera may carry out prior to entering into the human body. For example, the capsule camera may perform a self-diagnostic to ensure that the system is fully functional. In addition, a reusable capsule camera may also communicate the number of times the capsule camera has been used inside a human body, so as to avoid introducing a capsule camera beyond the number of times it is designed to be used for. Alternatively, the capsule camera may be disposable (i.e., used only once).

From the mouth, the capsule camera enters the esophagus, then the stomach, the small intestines and the large intestines, in that order, before exiting the body. After it exits the body, no more images need to be taken. To image the large intestines, motility-enhancing drugs are typically used, so that the capsule camera may be able to traverse the entire GI tract within a reasonable amount of time, and particularly before the power needed for its operations is exhausted. In other words, it is desired that some power remains at the time the capsule camera exit the body. To cover the expected variations within the human population, the capsule camera must be provided power to allow a complete imaging for a very high percentage of people. Therefore, for most people, many images are taken by the capsule camera even after the capsule exits the body.

The storage requirement for the images is one problem current capsule endoscopy must overcome. The large size of a file created from the images taken from a human person is prohibitive for transmission over the Internet, and makes archiving and later retrieval difficult and costly. Another problem is cost. To have a technician review and edit out images in the file that are taken outside of the human body is costly. Further, a patient should be able to use the capsule camera at his/her home without privacy concerns, images taken outside the body should not be stored or transmitted.

Also, for a capsule camera in which on-board storage is provided for storing images, rather than transmitted by wireless, the capsule camera must be retrieved after it exits the body. A mechanism that facilitates retrieval after the capsule exits the body is desirable.

In light of the above, an automatic method for detecting when the capsule enters into and exits the body is desired, together with the ability for the capsule camera to distinguish its various modes of operations are desired.

SUMMARY

According to one embodiment of the present invention, a method for detecting a capsule camera entering into or exiting the GI tract, includes (a) taking a first test image under the condition that an illumination system of the capsule camera is disabled; (b) taking a second test image under the same condition as the first test image; (c) comparing selected corresponding pixel values of the first test image and the second test image to determine if a significant change in pixel values has occurred; and (d) upon detecting the significant change in pixel values, determining if the capsule camera has entered or exited the GI tract, and performing operations appropriate to follow such determination. It is possible to detect entering or exiting the patient's body using a single exposure rather than two because, if the LED's are off, the pixel intensities detected by the camera inside the body are very low. A threshold can be set, for example, above which the capsule camera is deemed detected to be outside the patient's body. Similarly, a threshold can be set below which the capsule camera is deemed detected to be inside the patient's body.

The appropriate operations performed after detecting the capsule camera's exit from the GI tract includes stopping further taking or storing of images and, optionally, activating an audio signal to indicate the capsule camera has exited the GI tract. The appropriate operations performed after detecting the capsule camera's entering into the GI tract may includes entering into an imaging mode for a next section of the GI tract, which may be the esophagus.

According to one embodiment, the test image is exposed on an image sensor array. In some implementations, only a selected portion of the image sensor array is used in the comparing with the threshold. In addition, a power-on self-test may be performed after the capsule camera is readied for use, the self-test providing a visual report indicating its integrity. The visual report may include a lighting pattern generated by the illumination system of the capsule camera.

According to one embodiment of the present invention, the comparing step for determining the next stage of the capsule camera's travel is first taken after a predetermined elapsed time from detecting the capsule camera entering into the GI tract, or from detecting the capsule camera is powered on. The elapsed time may be empirically determined from statistics collected from a population of subjects whose GI tracts are imaged.

According to one embodiment of the present invention, the method may further include determining if a significant change in the capsule camera's operating environment has occurred, as measured by a secondary sensor, which may be a thermometer. The significant change may be detected by comparing a temperature measured by the thermometer against a predetermined range. The capsule camera may be calibrated under test conditions to determine the predetermined range. The calibration reduces or eliminates a difference in temperature between the capsule camera and the GI tract by compensating for the capsule camera's operations. The calibration results are recorded in a storage device in the capsule camera for subsequent retrieval for detection operations. In another embodiment, the significant change is determined by comparing two or more temperature measurements taken at different times.

According to one embodiment of the present invention, the thermometer may include a first set of one or more devices connected in series with a second set of one or more devices, wherein the first set of devices have a different temperature dependence than the second set of devices. The first set of devices may be one or more short channel transistors, and the second set of devices may be one or more long channel devices. Alternatively, the first set of devices are each biased to operate within a linear region, and the second set of devices are biased to operate in a saturation region. A digital-to-analog converter may be provided to sense a voltage at an electrical node between the first set of devices and the second set of devices. In one embodiment, the first and the second set of devices operate with a strong inversion layer.

Alternatively, the thermometer may operate by measuring a leakage current across a PN junction. To measure the leakage current, the PN junction is precharged by applying a reverse bias voltage across the PN junction. The leakage current loss is measured by a voltage of the PN junction after a predetermined time period.

According to another aspect of the present invention, a capsule camera includes (a) an illumination system providing light to illuminate a field of view of the capsule camera; (b) a sensor array for taking an image by capturing the light from the illumination system reflected from objects in the field of view; (c) an image processing unit processing the images from the sensor array for subsequent review; and (d) a clock generation module providing one or more clock signals to operate the image processing unit; and (e) a control unit controlling a frequency of operation of the clock signals in response to a control signal derived from an output signal of a sensor. The output signal may be provided from the sensor array under a test condition, or from a secondary sensor, such as a thermometer. In one embodiment, the capsule camera further includes an enabling logic circuit for providing one or more enable signals for enabling and disabling DC paths in one or more of the illuminating system, the sensor array, and the image processing unit.

The present invention is better understood upon consideration of the detailed description below in conjunction with the drawings.

BRIEF DESCRIPTION OF THE DRAWINGS

FIG. 2A is a block diagram 200 of capsule camera 100 of FIG. 1A, having onboard storage 18 to store the images.

FIG. 2B is a block diagram 240 of capsule camera of FIG. 1B, having wireless transmitter and antenna system 30 for transmitting image data to an external receiver (not shown).

To facilitate cross-referencing among the figures, like elements in the figures are assigned like reference numerals.

DETAILED DESCRIPTION OF THE INVENTION

Figure 1A:
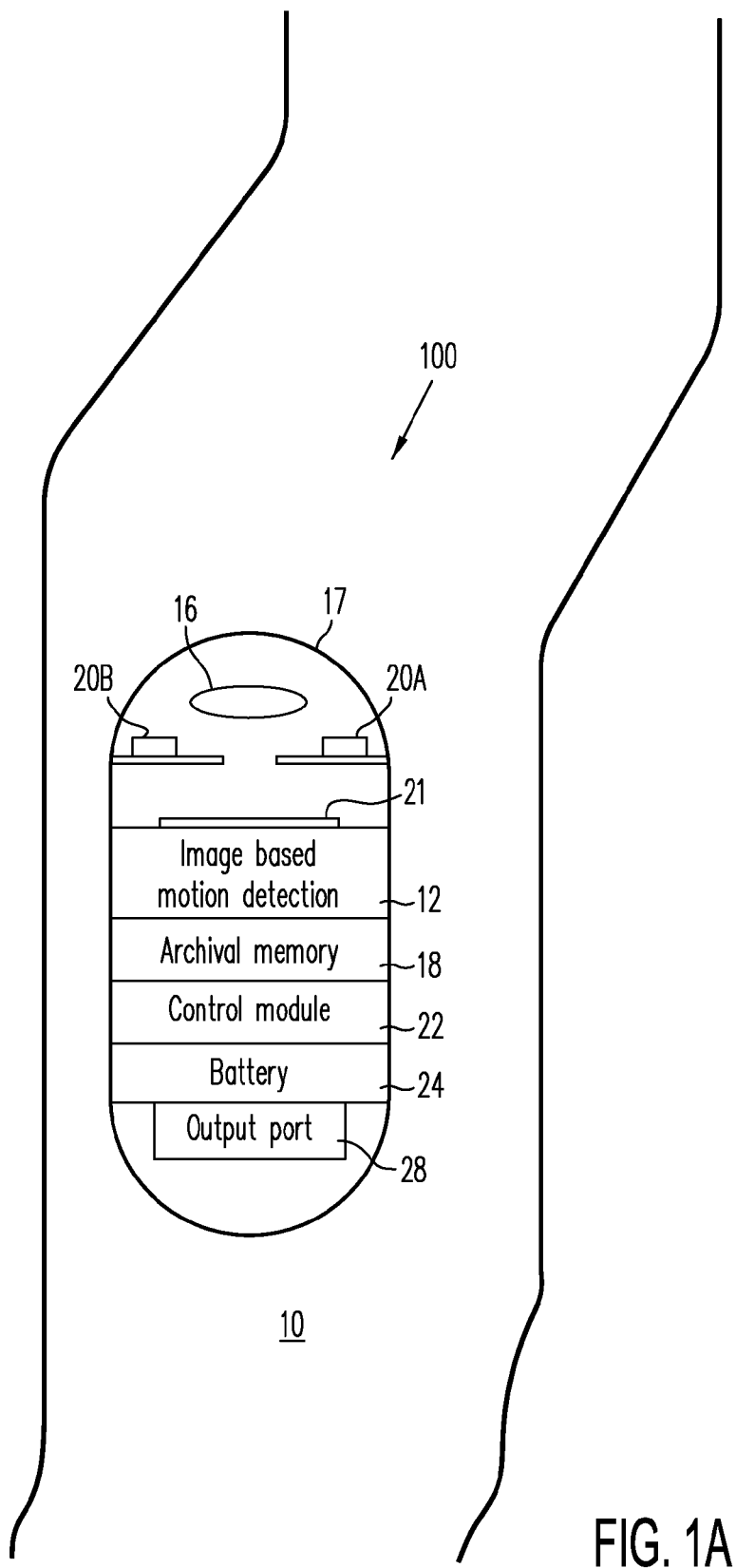
FIG. 1A shows schematically capsule camera 100 inside a gastrointestinal tract 10 taking measurements; capsule camera 100 stores images taken in its on-board archival storage system.

FIG. 1A shows capsule camera 100 taking measurements inside gastrointestinal tract 10. As shown in FIG. 1A, capsule camera 100 includes housing 17, optical system 16, LEDs 20A and 20B, and image sensor 21. Image sensor 21 may include one or more sensor array. The image captured by image sensor 21 is processed by image processor 12 using digital signal processing techniques. In addition, to conserve storage space and power, image processor 12 may also compare successive images taken and selects for storing in archival memory or storage system 18 only those images that are sufficiently different from their immediate predecessors. Images may be compressed to save storage space. Power supply 24 provides power for capsule camera 100's operations. Control unit 22 controls the operations of all functional units in capsule camera 100. After capsule camera 100 is recovered, output port 28 allows a user to upload to a workstation the stored images and other data.

Figure 1B:
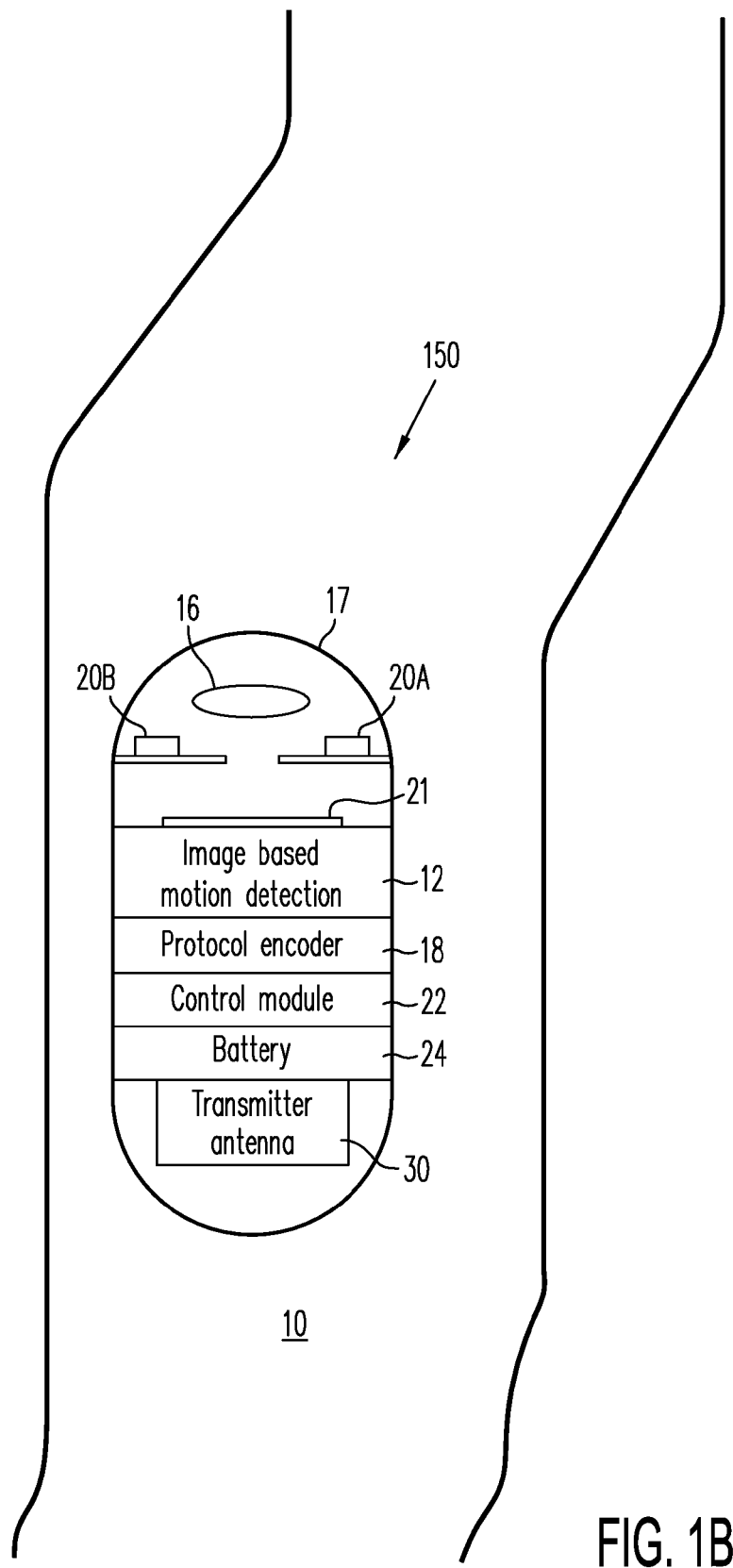
FIG. 1B shows schematically a variation of the capsule camera in FIG. 1A: capsule camera 150, of FIG. 1A.

FIG. 1B shows schematically capsule camera 150, which is a variation of capsule camera 100 of FIG. 1A. In FIG. 1B, instead of storing the images on-board, transmitter and antenna system 30 is provided in capsule camera 150 for transmitting image data to a receiver outside of the patient's body, where the image data may be processed or archived for later review. The present invention is applicable to both systems that store the image data on-board and systems that transmit the image data.

FIG. 2A is a block diagram of capsule camera 100 of FIG. 1A, having onboard storage 18 to store image data. FIG. 2B is a block diagram of capsule camera of FIG. 1B, having wireless transmitter and antenna system 30 for transmitting image data to an external receiver (not shown), which may then provide the image data to a data recorder. In FIGS. 2A and 2B, each capsule camera is shown to include LED drivers 210 that control LED illumination system 202 to illuminate a field of view for the capsule camera. Imaging optics system 203 collects and focuses the reflected light onto image sensor 204. In FIG. 1A or 1B, motion detection module 205 examines the images taken to determine whether or more motion has occurred between images. If motion does not occur between two successive images, the redundant image is not stored or transmitted. In FIG. 2B, protocol encoder 207 is provided to encode the image data for transmission in transmission and antenna system 30. Control unit 22, shown in each of FIGS. 2A and 2B, controls the operations of the capsule camera.

FIGS. 2A and 2B each also show secondary sensor system 206. Secondary sensor system 206 may include, for example, a pH meter for measuring the acidity of the GI tract. Such a pH meter has been successfully used, for example, since the famous Heidelberg capsule. Other example of a secondary sensor that may be used is a thermometer for measuring the body temperature.

Figure 3A:
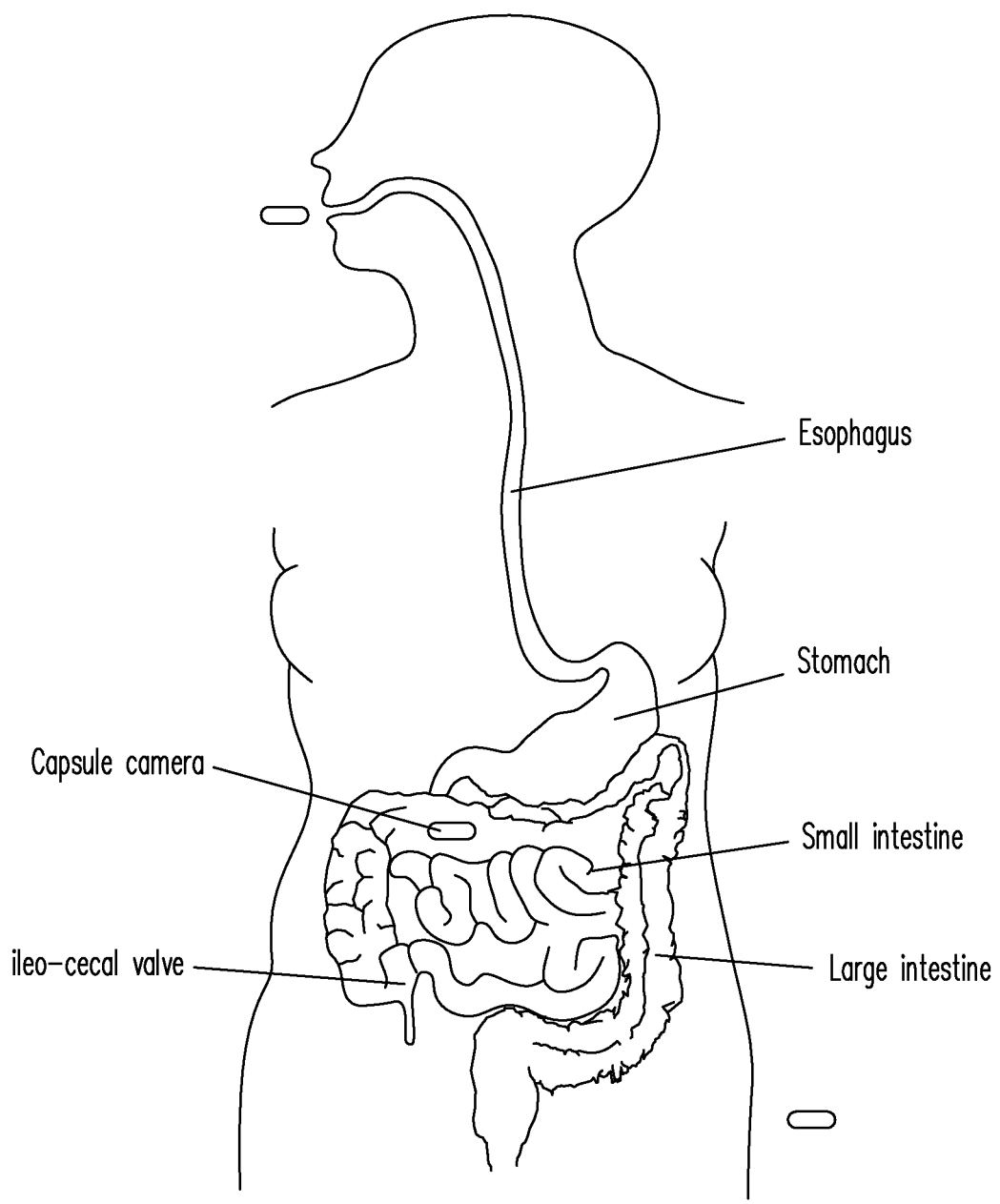
FIG. 3A shows a capsule camera being applied to a human subject.
Figure 3B:
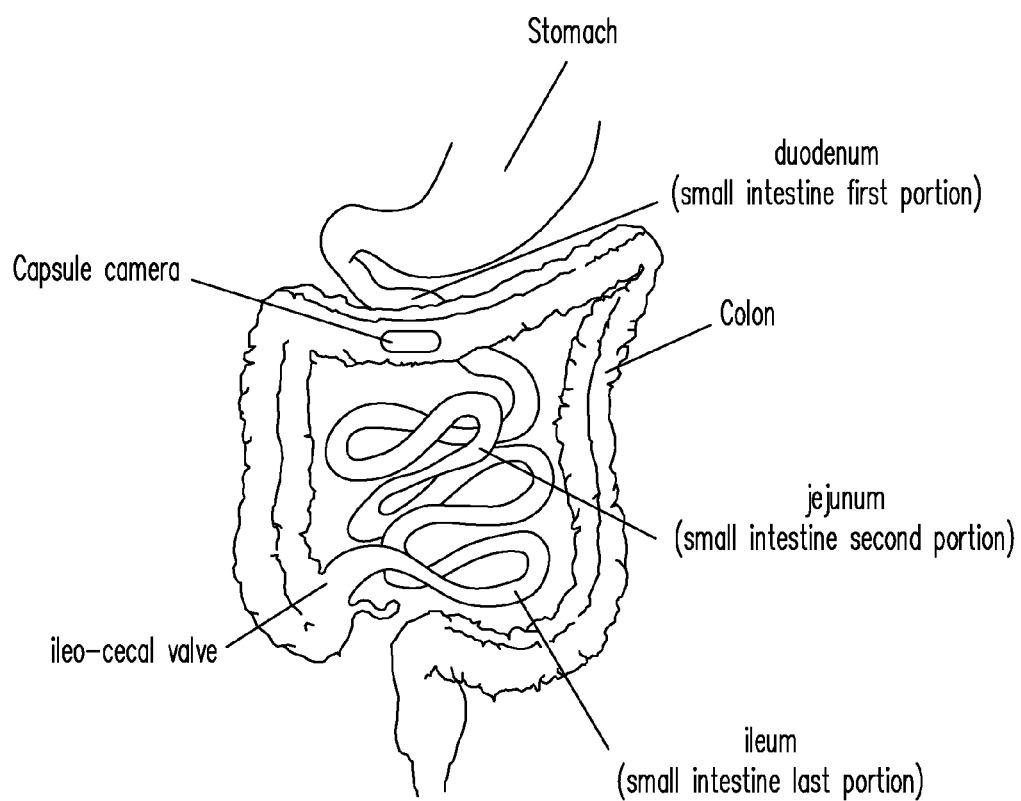
FIG. 3B shows a capsule camera in the colon region of the GI tract, having left the stomach and small intestine regions.

FIG. 3A shows a capsule camera being applied to a human subject. The capsule camera is swallowed and passes through the body by peristalsis. Alternatively, the capsule camera may be helped along by a force transmitted from the outside to the capsule camera by magnetic induction, or by any other suitable force. After the capsule camera travels through the body, it is expelled by the body. A capsule camera with an on-board memory device for archival storage of the images is retrieved after use. A capsule camera that transmits the images as the capsule camera travels through the body need not to be retrieved after use. FIG. 3B shows a capsule camera in the colon of a human subject, having passed through the stomach and the small intestines. The human intestines are highly convoluted and pose difficulties for a tethered camera used as an endoscopic instrument for internal inspection.

Figure 4:
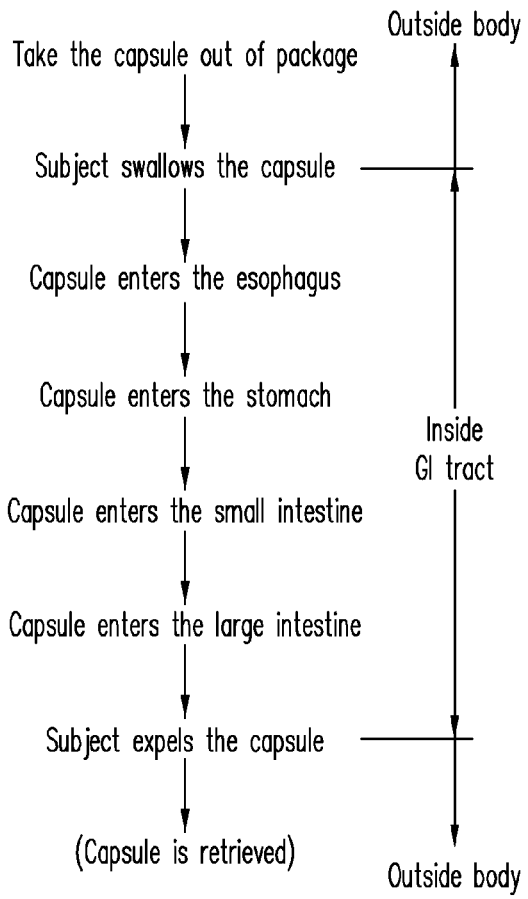
FIG. 4 shows different stages a capsule camera goes through in a typical endoscopic application on a human subject.

FIG. 4 shows different stages a capsule camera goes through in a typical endoscopic application on a human subject. The capsule camera may begin operation once it is taken out of the package (e.g., when a magnetically operated reed switch is closed by the act of removal from the package). The physician may be interested in examining the entire GI tract or selectively, for example, the esophagus and large intestines, or the small intestine only. However, for some high resolutions or frame rates, a capsule camera may be limited in power to target only a portion of the GI tract. In addition, the capsule camera may also be limited by the available on-board memory capacity, or another factor. The tens of thousand of images taken of each patient's GI tract per application limit the number of diagnosis a physician can make over a given time period. The large amounts of data make archiving, subsequent retrieval, and transferring patient histories among hospitals difficult and costly. A method that facilitates targeting only selected portions of interest in the GI tract saves effort, time and cost.

From the design point of view, a different set of device parameter values may be required for imaging each stage of GI tract. For example, (1) a capsule camera need not take images before being swallowed, (2) while a capsule camera storing images in an on-board storage device need not take images after it is expelled from the human body, it is required to be retrieved, so that a mechanism to facilitate retrieval (e.g., a audio beacon that indicates its position) is desirable; or (3) as the capsule camera moves faster in the esophagus than in another area of the GI tract, a much faster frame rate over a shorter duration is appropriate for the esophagus stage relative to another stage. Furthermore, a capsule camera may be provided an expandable balloon which, upon entering the large intestines, expands to stabilize the capsule. For such a system, the balloon expansion should occur only after the capsule camera is detected to have entered the large intestines. Severe adverse effects may result if the balloon is expanded in the small intestines. It is evident from these examples that a method for detecting the capsule camera's transitioning between stages allows both effective and efficient control of the capsule camera in each stage of the GI tract. Optimizing capsule camera operations is a significant objective from a total medical system solution implementation point of view.

Figure 5:
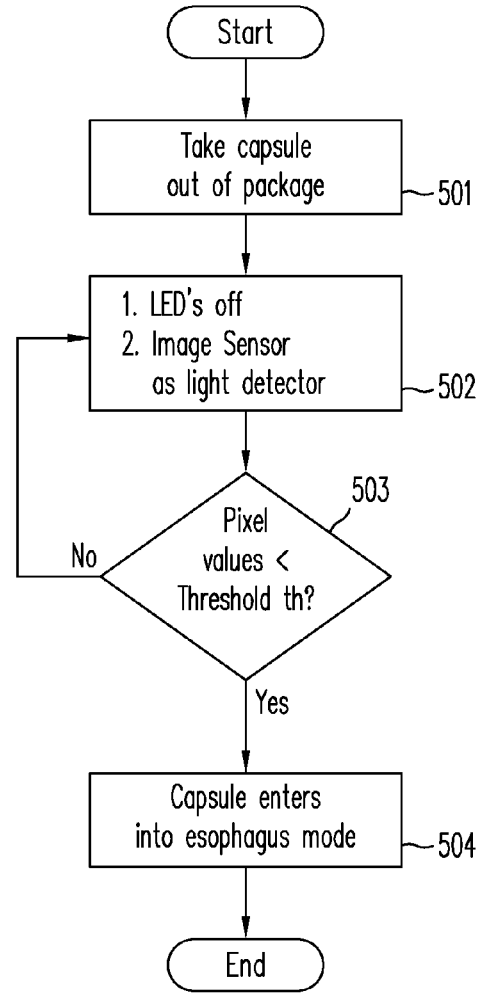
FIG. 5 shows flow chart 500 corresponding to a method for detecting a capsule camera entering an esophagus from the time the capsule camera is removed from a package, in accordance with one embodiment of the present invention.

FIG. 5 shows flow chart 500, corresponding to a method for detecting a capsule camera entering an esophagus from the time the capsule camera is removed from a package, in accordance with one embodiment of the present invention. The method of flow chart 500 takes advantage of the darkness in the esophagus when the LED's of the capsule camera are turned off. As described above, the capsule camera may be designed to be activated when it is removed from its package (e.g., step 501 of FIG. 5). As shown in FIG. 5, initially all the LED's are turned off, and the image sensor (e.g., image sensor 21 of FIG. 1A) in the capsule camera is configured to detect light without the LEDs illuminating the field of view (step 502). Once a selected set of pixel values—or other values derived from the pixel values (e.g., an average pixel value or a norm of the pixel values) are detected to be below a threshold value (step 503), the capsule camera enters into a mode suitable for operations in the esophagus stage (step 504). The selected set of pixels may be a pre-selected subset or the entire image.

Figures 6, 7:
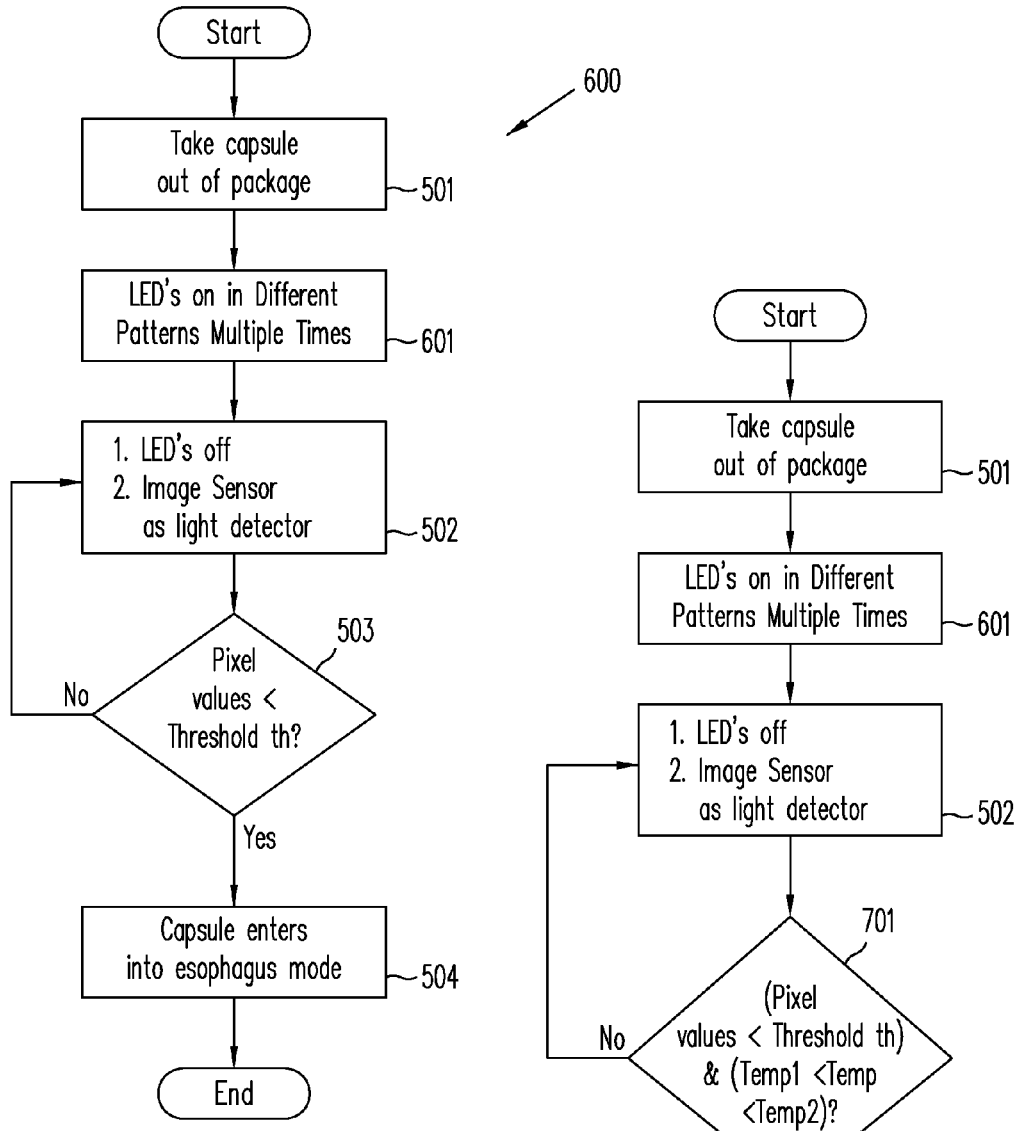
FIG. 6 shows flow chart 600, corresponding to a method in which a capsule camera indicates a successful powered-on self-test by flashing its LED's according a predetermined pattern, in accordance with one embodiment of the present invention.
FIG. 7 shows flow chart 700, in which the image sensor and a temperature sensor are both used to detect the condition at which the capsule camera enters the esophagus (step 701), in accordance with one embodiment of the present invention.

FIG. 6 shows flow chart 600, corresponding to a method in which a capsule camera indicates a successful power-on self-test by flashing its LED's according a predetermined pattern (step 601), in accordance with one embodiment of the present invention. Under this method, the magnetically operated reed switch (i.e., power switch) in the capsule camera is put in the "off" state every time the capsule camera returns to its package where a magnet field is present. Each time the capsule camera is removed from the package, a power-on self-test is performed. The results of the self-test (e.g., all systems operational, or one or more error conditions are detected) is reported by the flashing pattern of the LEDs. In addition, after the reed switch has been closed for a predetermined period of time, the capsule camera may record in a nonvolatile storage device (e.g. in a flash memory) the number of times the capsule camera device has been used (by incrementing the previous stored number of times of use). This number of times may be reported before ingestion by a flashing pattern of the LEDs. (For example, a suitable flashing pattern may require some LEDs to stay "off," or be turned on and off in a predetermined sequence or power levels). Such information for preserving the capsule camera's history in the non-volatile way described above may also be based on a detection of the capsule camera entering or exiting the human body using, for example, one of the methods described below.

Under the method of FIG. 6, the operations of the capsule camera after the power-on self-test are substantially those discussed above with respect to FIG. 5, and are therefore not repeated. For a capsule camera with a non-volatile archival memory, the capsule camera may retrieve historical information concerning the capsule camera ("device history") from the archival memory. The pattern signaled by the LED's may be different dependent on the device history. The device history may also limit the operations that can be performed by the capsule camera (e.g., if a capsule camera has been used once before in a human body, health regulations may prohibit its used for taking images of the GI tract again; alternatively, the capsule camera may be required to operate in a different way than a brand new capsule). Control unit 22 may retrieve the device history at power-up to control subsequent device operations accordingly. Even for a capsule camera with a wireless transmitter and antenna, a device history may stored in an on-board storage device; of course, such as storage device need only have a much smaller in capacity than a storage device used for archiving images.

Because the temperature in the esophagus is within a well-known range (i.e., 36° C. to 43° C.), a temperature sensor (e.g., a temperature sensor in secondary sensor 206 of FIG. 2A or 2B) maybe used to detect the capsule camera's entry into the esophagus mode. FIG. 7 shows flow chart 700, in which the image sensor and a temperature sensor are both used to detect the condition at which the capsule camera enters the esophagus (step 701), in accordance with one embodiment of the present invention. The other steps in the method of flow chart 700 are substantially those of FIG. 6, and their descriptions are therefore omitted for brevity. As the capsule camera dissipates some amount of power during its operations, the temperature in the capsule camera may be slightly higher than the esophagus. However, as the esophagus—which is composed primarily of tissue and water—is an effective thermal conductor, such that only a small value need be added to the 36° C. to 43° C. range in the empirical data to account for any heating of the capsule camera due to the capsule camera's operation. The added value depends on the operational parameters, e.g., the frame rate, the nature and the functions operating in the capsule camera, the illumination in each LED, and whether or not storage or transmission is performed.

Even though step 701 of FIG. 7 requires a comparison of temperatures, a thermometer that provides an absolute temperature may not be necessary. Instead, a temperature-dependent physical phenomena may be used which provides a measurable physical quantity that can be compared against a range of values (i.e., corresponding to a physical quantity having a value between Temp1 and Temp2, as illustrated by step 701 of FIG. 7). During manufacturing or any time before the subject swallows the capsule camera, the values corresponding to Temp1 and Temp2 are stored in the capsule camera. Inside the patient's body, the current value of the selected physical quantity is compared to the recorded values of Temp1 and Temp2 to determine if the current value is within the desired range. A number of different pairs of values for Temp1 and Temp2 may be provided for use under different operating parameters.

As described, the values Temp1 and Temp2 of FIG. 7 are adjusted for the temperature difference at the thermometer relative to the capsule camera's environment. As discussed above, the difference in temperature depends also on the thermal conductance between the capsule and the environment, the amount of heat generated in the operations and the heat distribution. Calibration may be carried out for different modes of capsule camera operations. For example, under an active mode, where pictures are taken with high LED intensities, for example, a substantial amount of heat is generated over a longer duration, relative to a monitor or stand-by mode of operation. Thus different temperature ranges (i.e., different values for Temp1's and Temp2's) may be stored in different parameter value sets, each parameter set being designed for use in predetermined operating conditions.

Alternatively, measurements may be made between operations to minimize the temperature difference between the capsule and its environment. In one embodiment, the values of Temp1 and Temp2 take into account operational parameters and the elapsed time since the operations are carried out. Of course, a lesser weight is provided to operational conditions which have taken place a greater elapsed time ago.

In one embodiment, temperatures are compared in the analog domain using an analog comparator. In one embodiment, regardless of whether the thermometer is junction-based or transistor-based (see discussion relating to FIGS. 9-12 below), the thermometer is located a distance DL away from the rest of the circuits on the integrated circuit. In one embodiment, DL is substantially greater than TW, where TW is the wafer thickness. (TW is a value typically around 300 μm after grinding.) By this arrangement, temperature increases due to operations of other circuits on the same capsule camera integrated circuit may be minimized, especially when the capsule camera integrated circuit is not packaged (e.g., as in a chip-on-board (COB) mounting). In one embodiment, the thermometer is provided its own power and ground pads, or isolated fixed voltage sources, so as to avoid noise and to provide greater accuracy.

To measure temperature, a thermometer takes advantage of a temperature-dependent material property or physical phenomena. The stronger the temperature-dependence, the more sensitive—and in general, the better—is the resulting thermometer. For example, a cubic or an exponential dependence allows a more sensitive instrument to be built than a linear dependence. Conversely, a square root or a logarithmic dependence results in a less sensitive instrument relative to a linear dependence. In that regard, the thermal leakage current of a semiconductor PN junction has a temperature dependence that is approximately proportional to $1/T \, e^{-1.1/nkT}$, where k is Boltzmann's constant, T is the absolute temperature, and n is a value between 1 and 2. At room temperature (i.e., 25° C.), kT is about 0.026. Thus, over the typical operating temperature range specified for a commercial semiconductor product, the PN junction leakage current varies over approximately three orders of magnitude. Thus, the leakage current of a PN junction exhibits strong temperature dependence. Accordingly, temperature may be measured from a loss of voltage at a pre-charged PN junction after a predetermined elapsed time. Some thermometers that are based on measuring a leakage current of a PN junction are shown in FIGS. 8A, 8B, 8C and 8D.

Figure 8A:
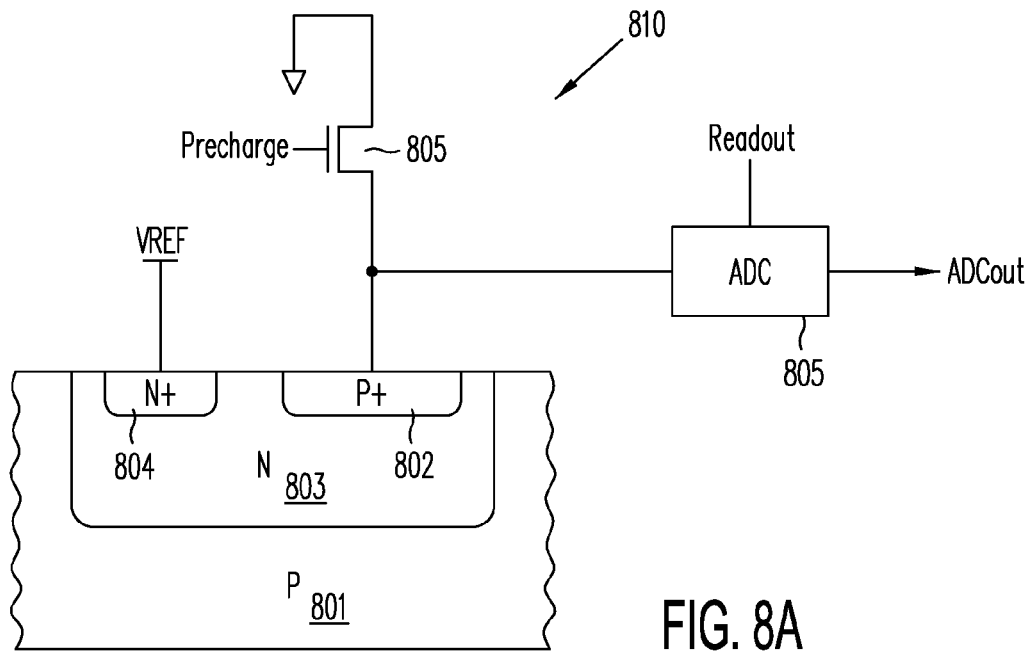
FIGS. 8A, 8B, 8C and 8D show, respectively, PN junction thermometers 810, 820, 830 and 840.

FIGS. 8A, 8B, 8C and 8D show PN junction thermometers 810, 820, 830 and 840, respectively. As shown in FIG. 8A, a P+N junction is formed in P-substrate 801 by P+ region 802, N-well 803 and N+ contact region 804. A positive bias voltage $V_{REF}$ is applied to N+ contact region 804 (and hence N-well 803 also) to reverse-bias the P+N junction. Initially, the pre-charge signal at the gate terminal of NMOS transistor 805 is turned on for a proper duration to pull P+ region 802 towards the ground voltage, such that the reverse-bias of the P+N junction is $V_{REF}$ volts. The Pre-charge signal is then turned off, and the charge stored in the P+N junction is allowed to leak. After a predetermined time period, the "Readout" control signal at analog-to-digital converter (ADC) 805 is asserted to sense the voltage on P+ region 802, which is now a voltage higher than ground, due to positive carriers (i.e., the holes) leaking into P+ region 802, while the negative carriers (i.e. the electrons) leak toward N-well 803 and the $V_{REF}$ node at N+ region 803. The measured rise in voltage at P+ region 802 is dependent on the temperature, as described above.

Figure 8B:
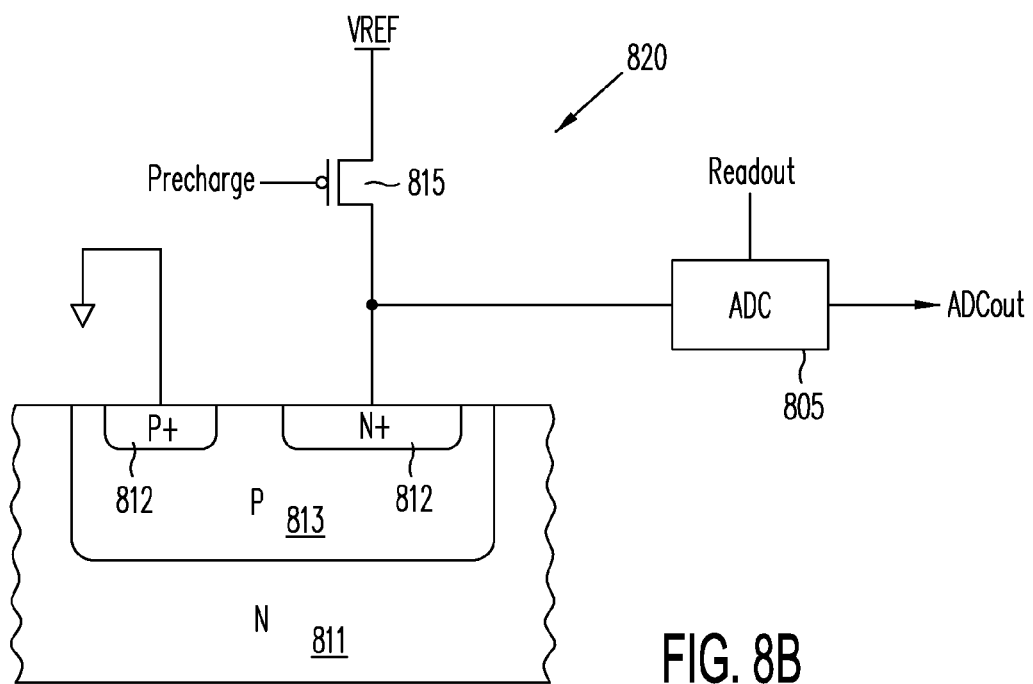
Figure 8C:
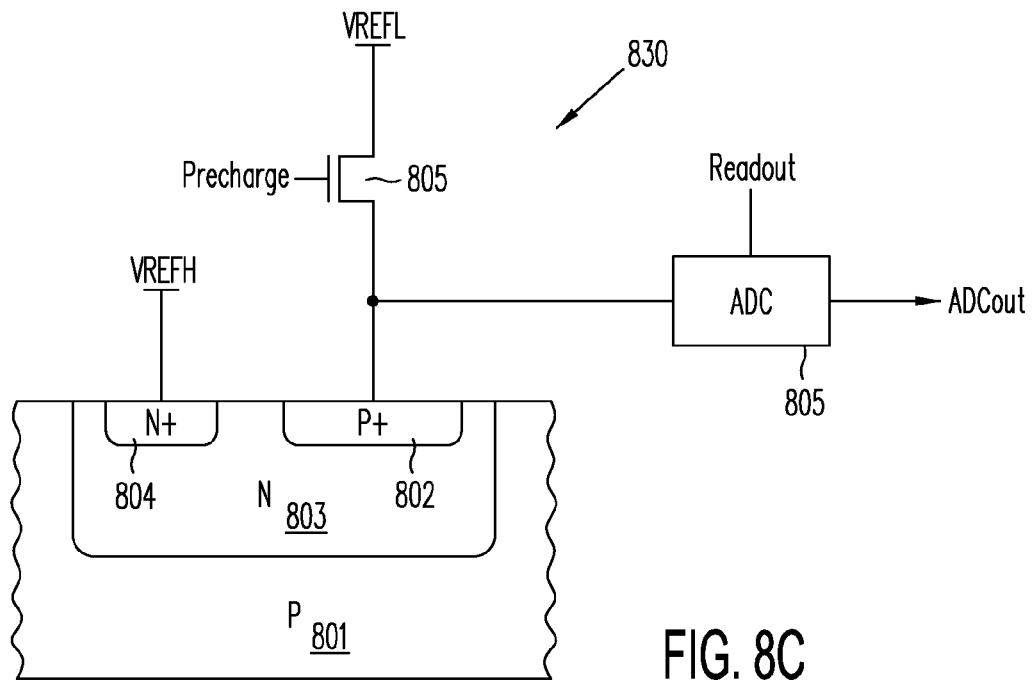
Figure 8D:
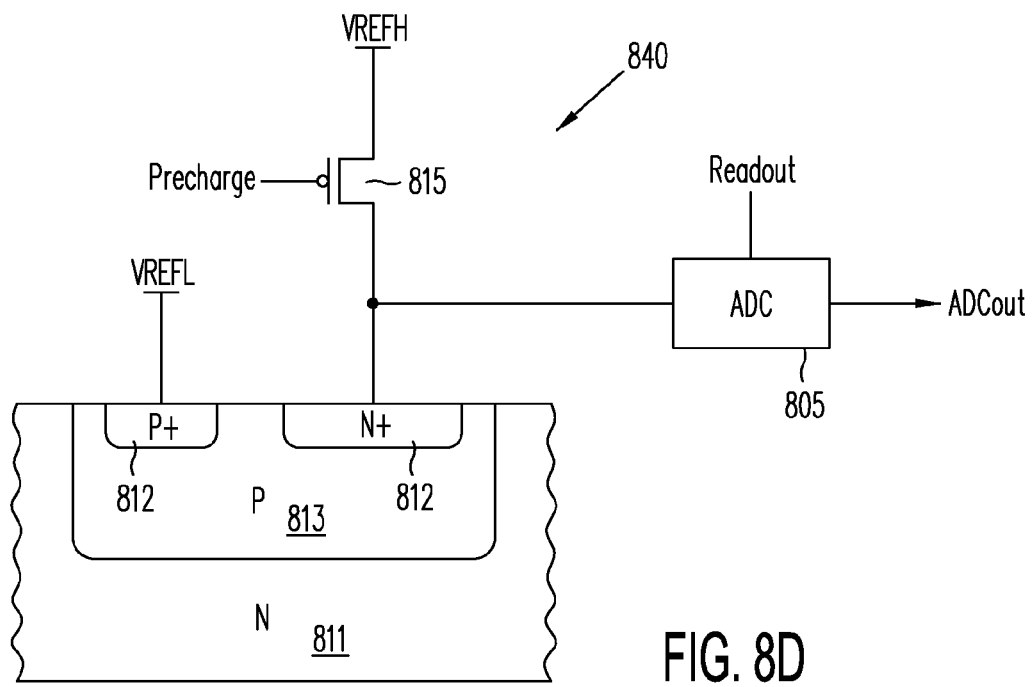

As long as a P region is enclosed by an N region (e.g., a P+ region provided inside an N region), which is further enclosed by another P region, a junction that can be used as a thermometer may be formed. FIGS. 8B, 8C and 8D show other configurations of such thermometers. For example, in FIG. 8B, a PN+ junction is formed in N substrate 811 which includes P+ contact region 814, P-well 813 and N+ region 812. The PN+ junction is pre-charged through PMOS transistor 815. In FIG. 8B, N+ region 812 is pre-charged to $V_{REF}$.

The thermometers of FIGS. 8A, 8B, 8C and 8D may be built using any semiconductor process. The $V_{REFL}$ and $V_{REFH}$ reference voltages of FIGS. 8C and 8D are just some suitable fixed voltage nodes having sufficient drive to accomplish the pre-charge. In FIGS. 8C and 8D, for example, P+ region 802 and N+ region 812 are pre-charged to $V_{REFL}$. Similarly, N+ region 812 is precharged to $V_{REFH}$. One advantage of using voltages $V_{REFL}$ and $V_{REFH}$, rather than between supply voltage $V_{REF}$ and the ground voltage, is to allow ADC 805 to operate more efficiently at this biasing point. In one embodiment, an N-channel transistor may be used to pre-charge the junction to the higher voltage (i.e., voltage VREFH, or voltage VCC); in that case, the junction voltage is at VREFH or VCC minus the threshold voltage of the pre-charge N-channel transistor. Similarly, a P-channel transistor may be used to pre-charge the junction to a lower voltage (i.e., voltage VREFL or GND); in that case, the voltage at the junction is VREFL (or GND) plus the threshold voltage of the pre-charge P-channel transistor. It may be also possible that, after the Readout sensing, a pre-charge is performed followed by another Readout sensing. In that case, a correlated double-sampling may be performed. An amplifier may also amplify the difference of the two sensed voltages.

In one embodiment, the pre-charge duration is provided at the beginning of a frame and the "Readout" duration is provided the end of the frame. In another embodiment, the pre-charge duration is provided at the beginning of a frame and the "Readout" duration is provided at the end of the frame, which may be N frames from the beginning of the pre-charge duration. A register or a parameter may be used to control the number of elapsed frames or elapsed time between the pre-charge and "Readout" operations. In one embodiment, ADC 805 is kept on all the time, while the "Readout" signal samples or latches the digital output.

Figure 12:
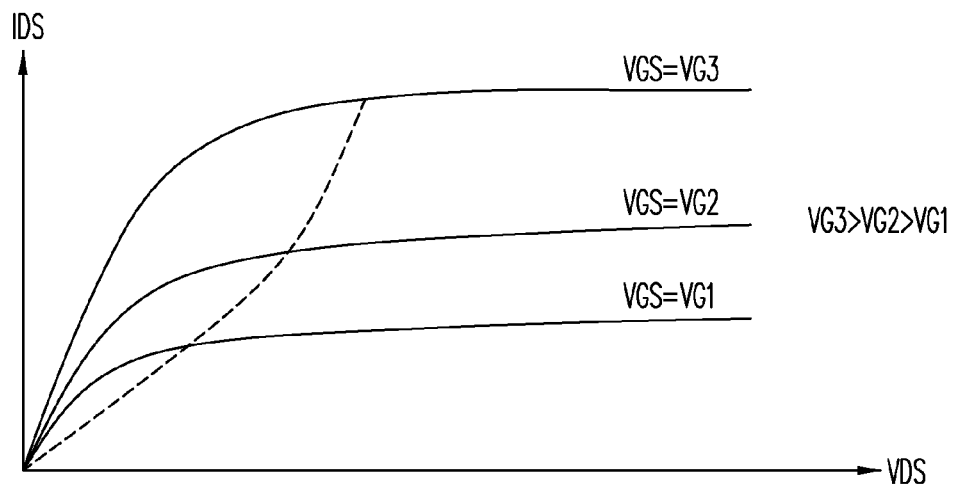
FIG. 12 shows a family of typical current-voltage curves for an N-channel transistor, in which IDS is the drain-source current, VDS is the drain-source voltage and VGS is the gate-source voltage.

FIG. 12 shows a family of typical current-voltage curves for an N-channel transistor, in which IDS is the drain-source current, VDS is the drain-source voltage and VGS is the gate-source voltage. As shown in FIG. 12, current IDS for each curve tends to flatten when drain-source VDS exceeds the "saturation voltage," which is marked for the family of curves by the dashed line. The region to the right of the dashed line is referred to as the saturation region, and the region to the left of the dashed line is referred to as the linear region. A similar family of curves exists for a P-channel transistor, but with proper polarity reversals. For each VGS, the current in the flattened part is referred to as the "saturation current."

Figure 9A:
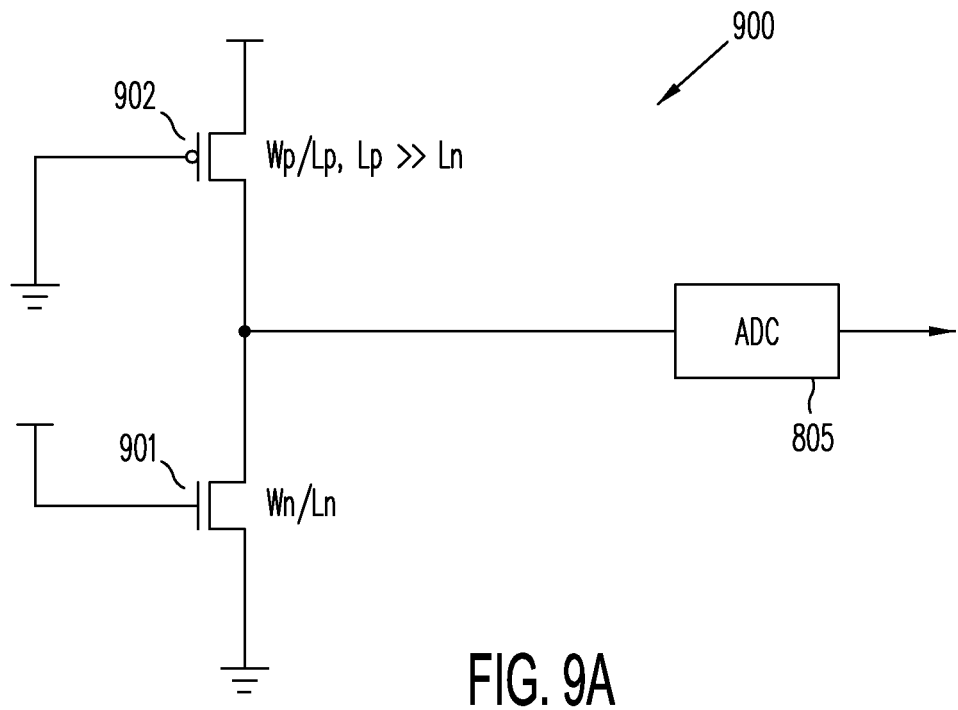
FIGS. 9A and 9B show semiconductor transistor thermometers 900 and 950, respectively.
Figure 9B:
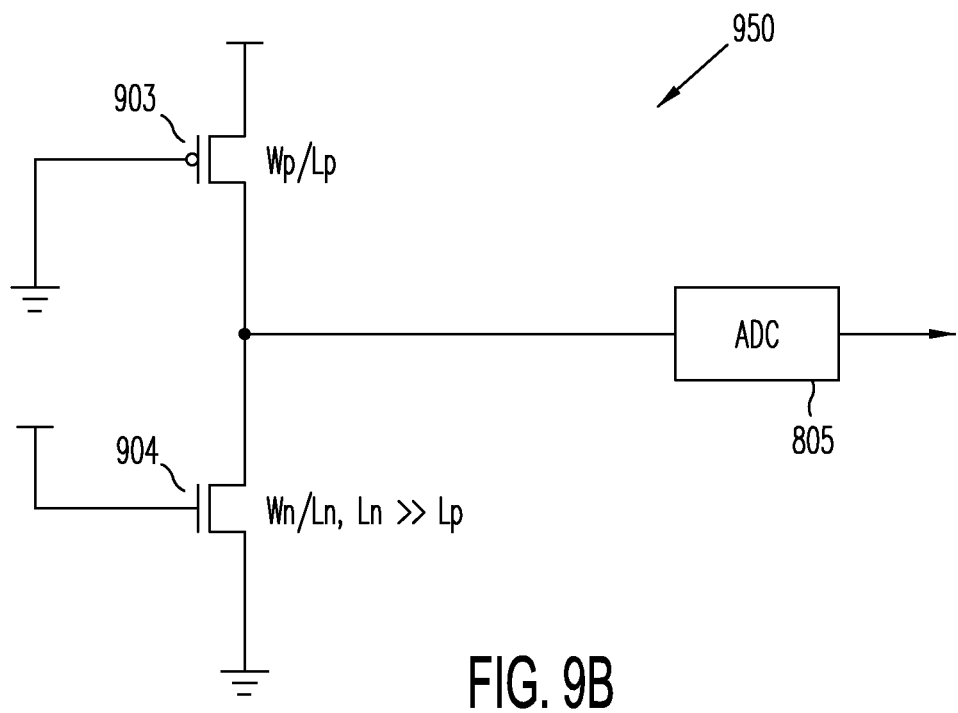

In a long-channel transistor, the temperature-dependence of the saturation current is approximately proportional to the square of the inverse of the temperature (i.e., $T^2$). In a short-channel transistor, however, the predominant physical mechanism for current saturation is carrier velocity saturation, which has a temperature-dependence that is approximately proportional to the inverse of the temperature (i.e., $T^1$). The resulting saturation current temperature-dependence is therefore approximately proportional to $T^d$, where d is a number between 1 and 2, and close to 1.5. FIGS. 9A and 9B show semiconductor transistor thermometers 900 and 950, taking advantage of the channel characteristics of these transistors. As shown in FIG. 9A, semiconductor transistor thermometer 900 includes long channel PMOS device 902 and short channel NMOS device 901. NMOS device 901 has, for example, the minimum design channel length for a small geometry process (e.g., a deep submicron process, such as a process having 130 nm feature size). In semiconductor transistor thermometer 900, when temperature rises, the voltage at the input terminal of ADC 805 falls. Conversely, when temperature falls, the voltage at the input terminal of ADC 805 rises. The output value of ADC 805 may be calibrated to indicate the temperature at thermometer 900. FIG. 9B shows semiconductor transistor thermometer 950 as including short channel PMOS device 903 and long channel NMOS device 904. In semiconductor thermometer 950, when temperature falls, the voltage at the input terminal of ADC 805 rises. Conversely, the voltage at the input terminal of ADC 805 falls when temperature rises. The output value of ADC 805 may be calibrated to provide a read-out of the temperature at thermometer 900.

As seen in FIGS. 9A and 9B, each of semiconductor transistor thermometer 900 and 950 has a DC current flowing directly from a power supply terminal to a ground terminal. In order to minimize power dissipation due to this DC current, both transistor 901 in FIG. 9A and transistor 903 of FIG. 9B may be minimum width (i.e., widths $W_n$ of transistor 901 and $W_p$ of transistor 903 are minimum-widths for the manufacturing process).

Figure 10:
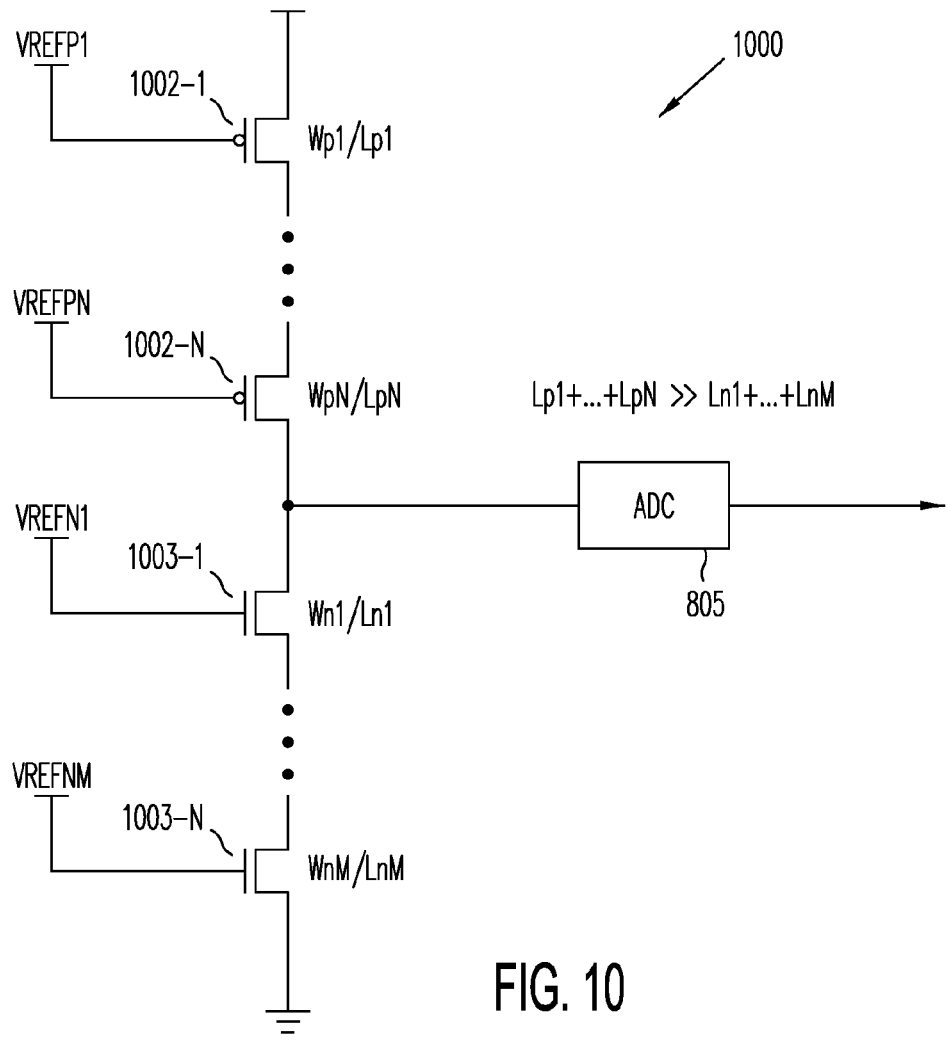
FIG. 10 shows generalized design 1000 for a transistor thermometer.

FIG. 10 shows generalized design 1000 for a semiconductor transistor thermometer, which includes a P-channel transistor chain (1002-1 to 1002-N) and a N-channel transistor chain (1003-1 to 1003-M). Transistor thermometer 1000 is the same circuit as transistor thermometer 900, when N=M=1. As shown in FIG. 10, because the sum of the channel lengths of all the PMOS devices is much greater than the sum of all the channel lengths of the NMOS devices (i.e., $Lp_1 + \ldots + Lp_N \gg Ln_1 + \ldots + Ln_M$) in the thermometer, the temperature dependence of the serially connected P-channel transistors is more pronounced than the temperature dependence of serially connected N-channel transistors. The gate voltage applied to each transistor may be different, so long as the transistor is turned on in the strong inversion region. In this case, the voltage at the input terminal of ADC 805 rises when temperature falls, and vice versa. Design 1000 is a generalized case for both semiconductor transistor thermometers 900 and 950 of FIGS. 9A and 9B.

Alternatively, the sum of the channel lengths of all the PMOS device may be selected to be much less than the sum of all the channel lengths of the NMOS devices (i.e., $Lp_1 + \ldots + Lp_N \ll Ln_1 + \ldots + Ln_M$). In that case, the temperature dependence of the serially connected N-channel transistors is more pronounced than the temperature dependence of the serially connected P-channel transistors, so that the input voltage to ADC 805 rises with temperature.

The thermometers of FIGS. 9A, 9B and 10 take advantage of the difference in temperature dependence between carrier velocity saturation and carrier mobility. Other temperature-dependencies may also be used.

In FIG. 10, each transistor may be formed by a number of parallel transistors, for example. Further, the source of first transistor in the P-channel transistor chain need not be connected to the power supply terminal, and the last transistor in the N-channel transistor chain need not to connect to a ground terminal. Any two voltage nodes providing an appropriate voltage difference such that all transistors are biased into the saturation region would suffice. The number of N-channel transistors may be limited to ensure a strong short channel velocity saturation effect is present. A circuit simulation (e.g., using the HSPICE simulation program) indicates the effect.

Figure 11:
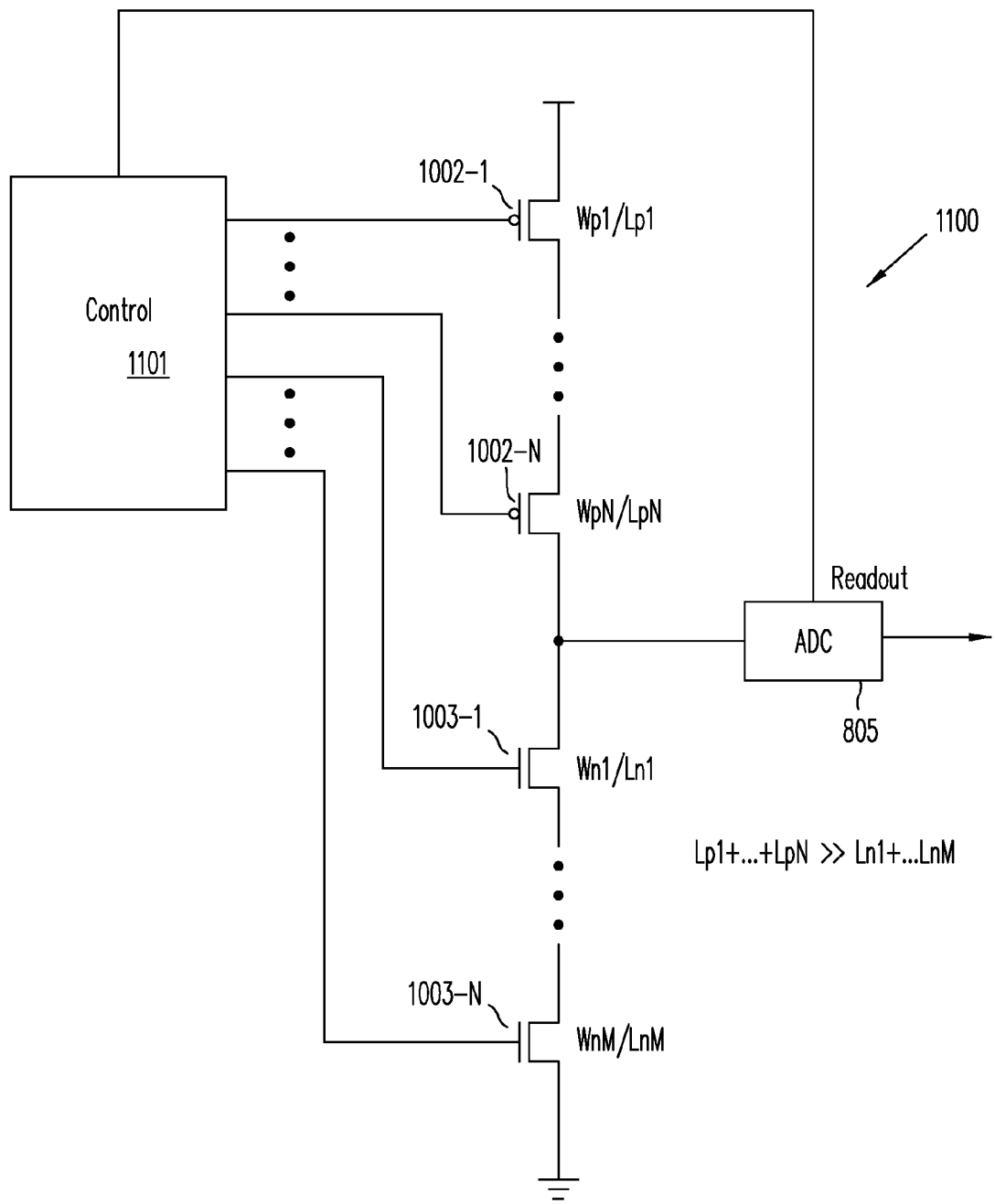
FIG. 11 shows transistor thermometer 1100, in which control circuit 1101 controls the gate terminals of P-channel transistor chain (1002-1 to 1002-N) and N-channel transistor chain (1003-1 to 1003-M) and to activate ADC 805 using the "Readout" signal at the time of temperature measurement.

FIG. 11 shows transistor thermometer 1100, in which control circuit 1101 controls the gate terminals of P-channel transistor chain (1002-1 to 1002-N) and N-channel transistor chain (1003-1 to 1003-M) and to activate ADC 805 using the "Readout" signal at the time of temperature measurement. (In practice, only one gate in P-channel transistor chain (1002-1 to 1002-N) or N-channel transistor chain (1003-1 to 1003-M) needs to be disabled to prevent a current flow.) Alternatively, ADC 805 may stay on, allowing the "Readout" signal to sample or latch the digital output signal of ADC 805.

One variation from the semiconductor transistor thermometer 900 of FIG. 9A is to provide both transistors 901 and 902 as short channel transistors, with one transistor being biased to operate in the linear region, while the other transistor is biased to operate in the saturation region. Since the saturation current (IDS) of a short channel transistor has a temperature dependence that is close to the power of −1.5, while the temperature dependence of the linear region current of the short channel transistor is close to the power of −2 (i.e., approximately the same as the temperature dependence of the saturation current in a long channel transistor), the resulting input voltage to ADC 805 rises with rising temperature in a circuit in which a N-channel transistor biased to operate in the linear region and a P-channel transistor biased to operate in the saturation region. Conversely, the resulting input voltage to ADC 805 falls with rising temperature in a circuit in which a P-channel transistor is biased to operate in the linear region and a N-channel transistor is biased in the saturation region. (A long-channel transistor has the same temperature dependence in the linear region as in the saturation region.) Similarly, if the transistors in one of the transistor chain of transistor thermometer 1000 of FIG. 10 meet the short channel requirement (i.e., all of $Lp_1, \ldots, Lp_N$ or $Ln_1, \ldots, Ln_M$ are short channel lengths) and are biased to operate in the saturation region, while the transistors in the other transistor chain of are biased to operate in the linear region, the difference between their temperature dependences may be exploited in a thermometer.

Referring back to FIG. 4, before the capsule camera enters into the patient's body, only the image sensor and the necessary image processing and controller functions are enabled. As the capsule camera's operation at this stage is relatively simple, the clock frequencies for carrying out these functions may be reduced. At this stage, none of the other functions (e.g., illumination by illumination system 202 except for the signaling after the self-test, compression, storage in archival memory 18, motion detection at module 205, or other functions) are performed. In one embodiment, the capsule camera does not cut off power to the circuits for performing these functions, because powering up these functions may cause significant delay in time and a power surge. Instead the input clock signals to circuits performing these functions are gated (i.e., the transitions in the clock signals are not propagated to these circuits) or significantly slowed, and DC paths are disabled. (A DC path is a current path between two nodes of different voltages, and which includes serially connected conducting transistors biased by a static gate voltage to operate with a strong inversion layer, i.e., VGS>VT+3kT, where k is Boltzmann's constant and T the absolute temperature. The static voltage on the gate terminals is non-varying (i.e., the derivative of gate-source voltage as a function of time is zero, or $$\frac{d(VGS)}{dt} = 0).$$

Normally, DC paths are disabled by deasserting enable signals in a module or for the entire integrated circuit. Alternatively, a chip select pin, CS or #CS, may be used.

Figures 13, 14:
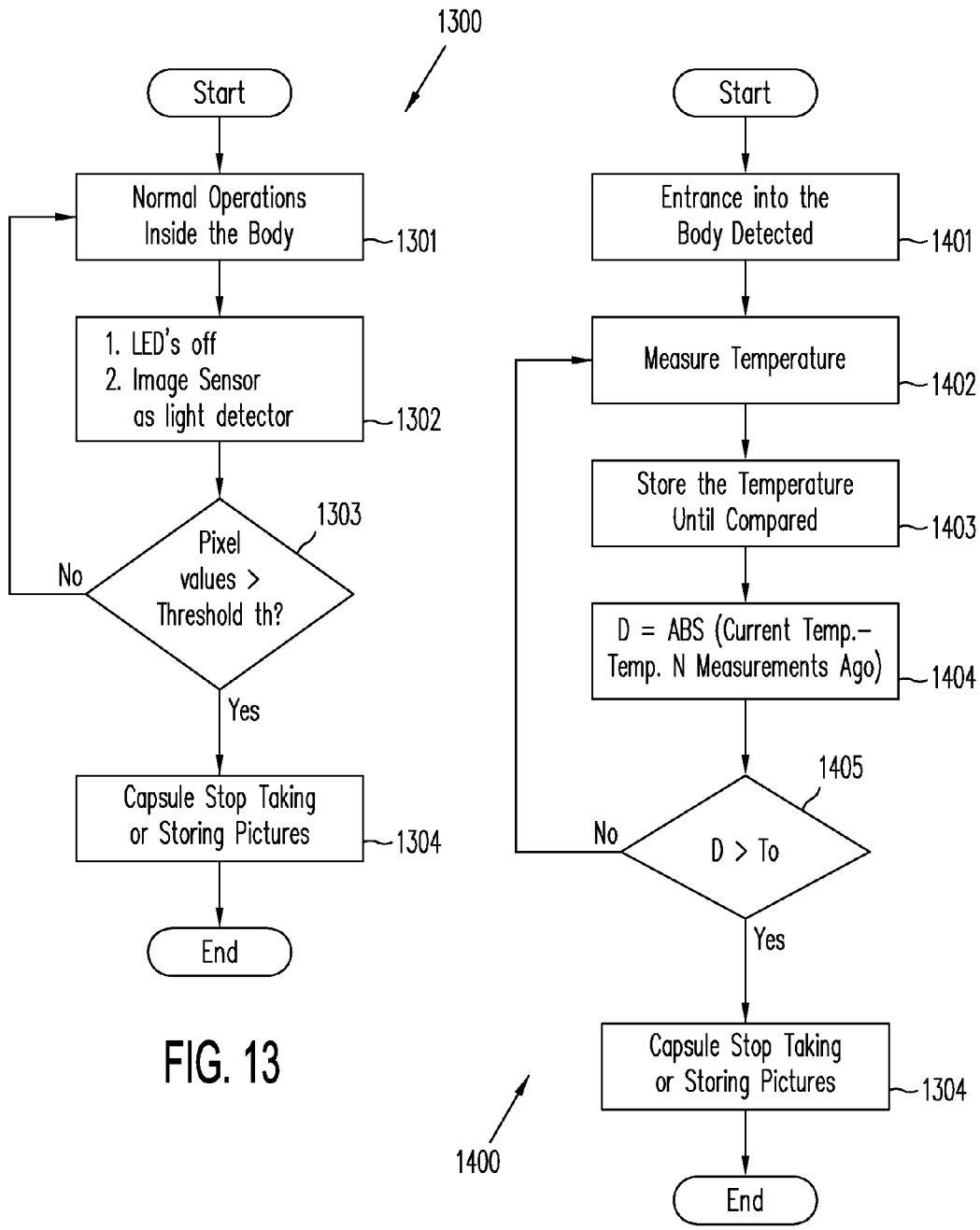
FIG. 13 shows flow chart 1300, corresponding to a method for detecting the exit of a capsule camera from the patient's body and the functions performed following detecting the exit.
FIG. 14 shows flow chart 1400, corresponding to a method which uses a thermometer to detect the exit of a capsule camera out of a patient's body, in accordance with one embodiment of the present invention.

FIG. 13 shows flow chart 1300, corresponding to a method for detecting the exit of a capsule camera from the patient's body and the functions performed following detecting the exit of the capsule camera from the body. During operations in a patient's body (step 1301), images may be taken without any illumination provided from the capsule (step 1302). At the end of the journey through the patient's body, if the capsule camera has exited the body, light is detected in some pixels on the image sensor array even though no light is provided from any illumination source within the capsule camera (step 1303). In one embodiment, the image taken covers only a fraction of an image sensor array. As the journey through the body is long, taking of these images without illumination need not start until after a predetermined elapsed time. The elapse time may be set by measuring, over a large number of subjects, the typical time the capsule camera stays in a patient's body. Motility-enhancing drug or other drug may be prescribed to affect the time for which the capsule camera may stay in the patient's body. Some care is required to determine the elapsed time to begin detecting exit from the patient's body, based on statistics collected from patients under similar medications. Alternatively, the elapsed time to begin taking images without illumination provided by the capsule may start after a predetermined time measured from the time the capsule camera was removed from its package (i.e., when the reed switch is activated).

For at least three reasons, the capsule camera must stop taking or storing images (step 1304) once the pixel values in an image for detecting exit exceed some predetermined threshold, indicating the capsule camera's exit from the body. First, image data collected up to this point may need to be transferred over the internet or be stored in a medium. As the battery (e.g., battery 24 of FIG. 1A) may still provide power beyond the capsule camera's exit from the patient's body, images are continued being taken and stored after the capsule camera exits from the body. The resulting file size may become significantly large, increasing the complexity, time, and cost for the transmission process or the storing process. The same problem exists also for wireless solution in FIG. 1B. This problem is especially probable for a large intestine diagnostic procedure. Second, if a technician is required to examine and to separate the images taken within the body from those taken outside the body, such a task adds significantly to the cost of the procedure. Third, for personal privacy protection reasons, a subject may prefer not to have others see images of his or her body taken after the capsule camera has exited his or her body. The recent proliferation of images and videos on the internet makes loss of privacy a legitimate concern. Thus, an additional step in method 1300 of FIG. 13 may include deleting images taken and stored following the last time the image sensor confirms that the capsule camera is still traveling through the body (i.e., the capsule camera did not detect light in an image that is not illuminated by capsule camera's illumination system). Deletion may also be made for a predetermined number of images taken and stored just before exit from the human body is detected.

FIG. 14 shows flow chart 1400, corresponding to a method which uses a thermometer to detect the exit of a capsule camera out of a patient's body, in accordance with one embodiment of the present invention. The method of FIG. 14 detects a sudden change in temperature to detect the capsule camera's exit from the body. Although an accurate temperature reading may be measured to detect a change in the capsule camera's operating environment, it is sufficient to merely detect a change in temperature that exceeds a predetermined threshold (steps 1404-1405). As discussed above, the temperature can be inferred from a measured physical quantity. The threshold may be experimentally determined (steps 1402-1403). For example, using a junction thermometer, a voltage difference may be compared with an experimentally determined threshold to determine if the capsule camera has exited the patient's body.

In FIG. 14, to determine a temperature change, the current measured temperature is compared with the last measured temperature (N=1; step 1404). Alternatively, the current measured temperature may be compared with a number of previously measured temperatures to detect a trend. Such a method would allow detection of both a fast exit and a relative slow exit from the body by the capsule camera. In one embodiment, the comparison is made using a measured temperature taken at a previous predetermined time point relative to the current time. In one embodiment, the current measured temperature is compared with multiple previous measured temperatures. Temperature measurements may begin following a predetermined elapsed time following closing of a reed switch in the capsule camera, indicating the capsule camera's removal from its package, or from the time the capsule camera is detected to have entered the human body (step 1401), using any of the previously described methods (e.g., the methods of FIGS. 5-7).

Because the GI tract inner wall radiates long-wavelength radiation in the red portion of the visible spectrum, one or more light detection operations or one or more temperature measurements, such as those used in the methods discussed above, may be made when a fall in radiation of those red portion of the visible spectrum is detected, relative to radiation from other portions of the spectrum. This test is probably more effective for detecting the capsule camera exiting the human body than entering.

Figure 15:
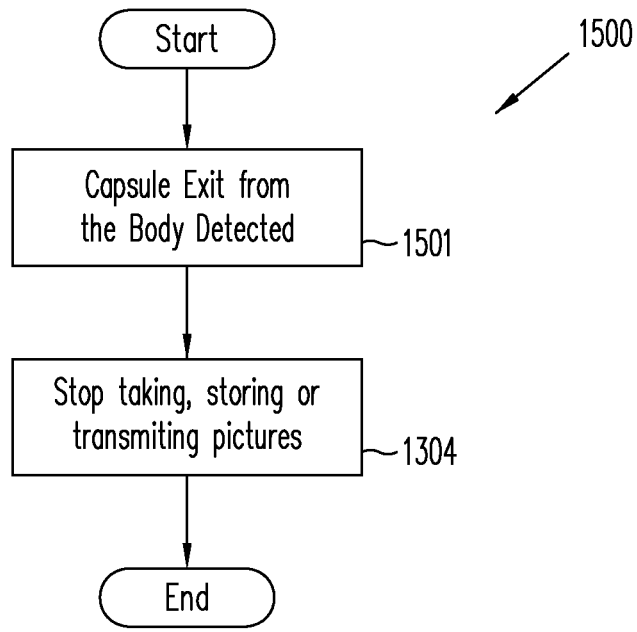
FIG. 15 shows flow chart 1500, corresponding to a method for detecting exit of a capsule camera; flow chart 1500 covers both a method practiced in a capsule camera which sends its images by wireless transmission (e.g., such as that in FIG. 1B) and a method practiced by a capsule camera which stores its images in a non-volatile archival memory (e.g., the capsule camera of FIG. 1A).

FIG. 15 shows flow chart 1500, corresponding to a method for detecting exit of a capsule camera; flow chart 1500 covers both a method practiced in a capsule camera which sends its images by wireless transmission (e.g., such as that in FIG. 1B) and a method practiced by a capsule camera which stores its images in a non-volatile archival memory (e.g., the capsule camera of FIG. 1A).

Figure 16:
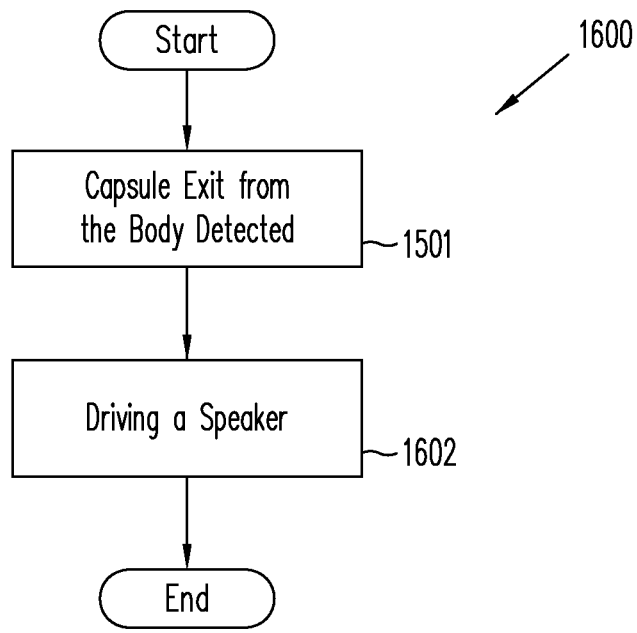
FIG. 16 shows flow chart 1600, corresponding to a method which drives a speaker in the capsule camera to provide an audible signal (step 1602) upon detecting the capsule camera's exit from the human body (step 1501).

FIG. 16 shows flow chart 1600, corresponding to a method which drives a speaker in the capsule camera to provide an audible signal (step 1602) upon detecting the capsule camera's exit from the human body (step 1501). The audible signal alerts the user and to facilitate retrieving the capsule camera to obtain the image data stored in the capsule camera's on-board memory. A suitable speaker may be a piezo-type speaker, or another suitable miniature speaker. In one embodiment, the pattern of sounds created may change after a predetermined elapsed time. Alternatively, the sound stop after a predetermined elapsed time.

Figure 17:
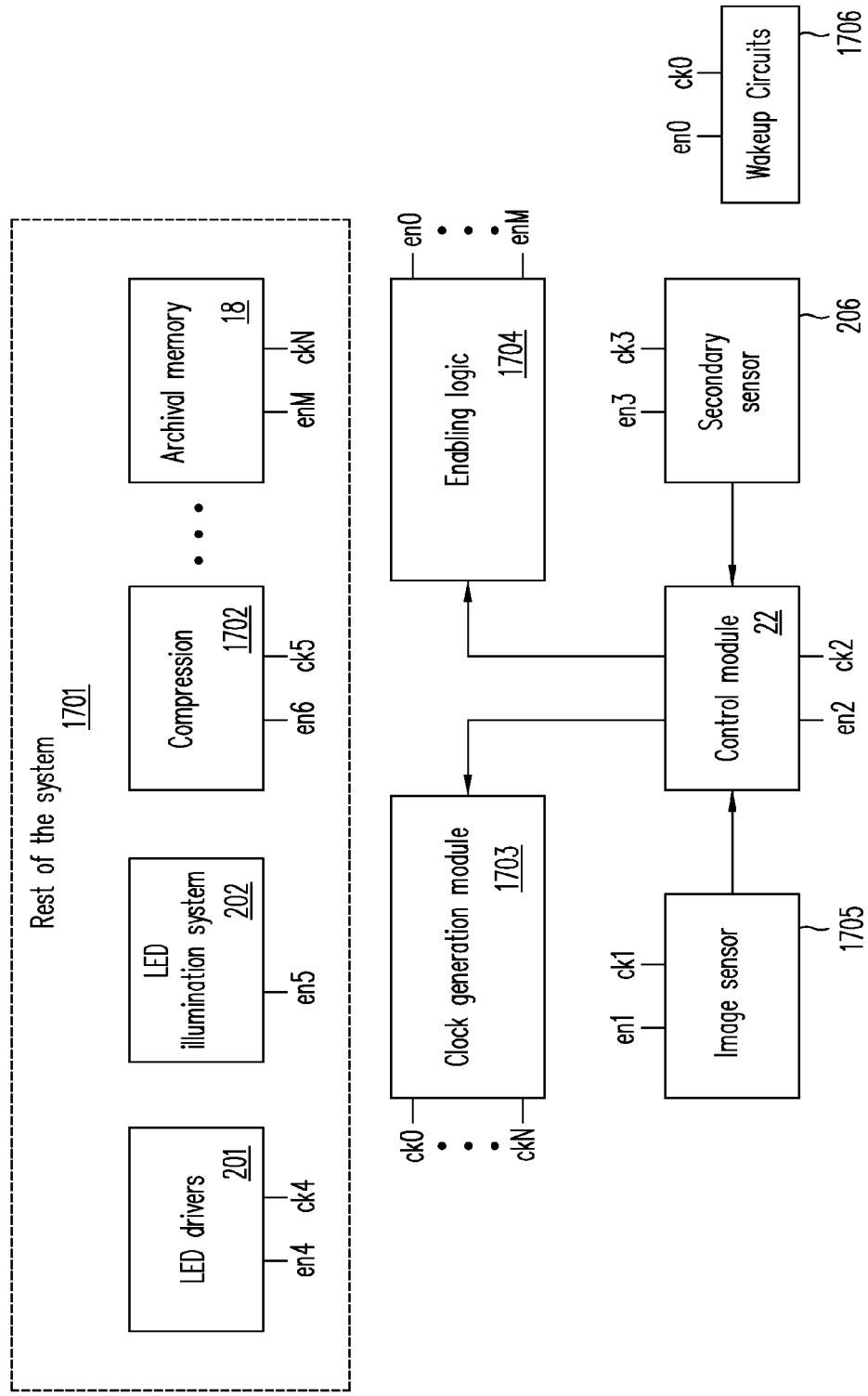
FIG. 17 is block diagram 1700 showing a capsule camera which is capable of power saving by means of slowing down or turning off clock signals to the different module, and selectively disabling DC paths, in accordance with the present invention.

FIG. 17 shows a control scheme in which clock signals ck0, . . . , ckN may be gated, or provided a much lesser frequencies, and enabling signals en0, . . . , enM may be disabled for every module (e.g., LED drivers 201, LED illumination system 202, compression module 1702 and archival memory 18), except wakeup circuits 1706, to preserve power and to wait for an event to wake up the capsule camera to perform a predetermined operation (e.g., when the exit of the capsule is detected). This power control scheme is useful for a capsule camera that stores its image data in an on-board memory, and which requires some power to keep data in a volatile memory until the capsule camera is retrieved. In that situation, a chip-enable or chip-select signal to the memory may be disabled and the memory enters a low-power data retention mode. Furthermore, some power may be needed the measurement related data, including image data, are downloaded to a workstation directly or through a docking system. The capsule camera may enter into a power-saving mode after activating an audio speaker for a predetermined time. Every module in FIG. 17 may not receive any clock signal or any enable signal. Some modules may receive multiple clock signals or multiple enable signals. (For example, in a module having static logic gates only, an enabling signal may not be needed.) Each enable signal turns off a DC path from the power supply reference to the ground reference when the input signals are not transitioning. Additionally, the system may include multiple resonant circuits or multiple crystal-driving circuits for clock system. In one embodiment, only the resonant circuit or the crystal-driving circuits for the wake-up circuits is kept on.

The above detailed description is provided to illustrate the specific embodiments of the present invention and is not intended to be limiting. Numerous variations and modifications within the scope of the present invention are possible. The present invention is set forth in the following claims.

I claim:

1. A capsule camera, comprising:
    an illumination system providing light to illuminate a field of view of the capsule camera;
    a sensor array for taking an image by capturing the light from the illumination system reflected from the field of view;
    an image processor processing the images from the sensor array for storage or transmission; and
    a clock generation circuit providing one or more clock signals to operate the image processor; and
    a controller controlling a frequency of operation of the clock signals in response to a control signal derived from an output signal of a sensor, wherein the output signal is provided from a secondary sensor which comprises a semiconductor-based thermometer that measures a leakage current from a PN-junction.

2. A capsule camera as in claim 1, further comprises an enabling logic circuit for providing one or more enable signals for enabling and disabling direct current (DC) paths in one or more of the illuminating system, the sensor array, and the image processor.

3. A capsule camera, comprising:
    an illumination system providing light to illuminate a field of view of the capsule camera;
    a sensor array for taking an image by capturing the light from the illumination system reflected from the field of view;
    an image processor processing the images from the sensor array for storage or transmission; and
    a clock generation circuit providing one or more clock signals to operate the image processor: and
    a controller controlling a frequency of operation of the clock signals in response to a control signal derived from an output signal of a sensor, wherein the output signal is provided from a secondary sensor which comprises a semiconductor-based thermometer that includes a transistor thermometer based on thermal characteristics of at least one P-channel transistor or at least one N-channel transistor.

4. A capsule camera as in claim 3, wherein the at least one P-channel transistor or the at least one N-channel transistor is long channel.

5. In a capsule camera, a method for power saving, comprising:
    providing an illumination system that provides light to illuminate a field of view of the capsule camera;
    providing a sensor array that takes an image by capturing the light from the illumination system reflected from the field of view;
    providing an image processor that processes the images from the sensor array for storage or transmission; and
    providing a clock generation circuit that provides one or more clock signals to operate the image processor; and
    controlling a frequency of operation of the clock signals in response to a control signal derived from an output signal of a sensor, wherein the output signal is provided from a secondary sensor which comprises a semiconductor-based thermometer that measures a leakage current from a PN-junction.

6. A method as in claim 5, further comprising providing one or more enable signals for enabling and disabling direct current (DC) paths in one or more of the illuminating system, the sensor array, and the image processor.

7. A method, comprising:
    providing an illumination system that provides light to illuminate a field of view of the capsule camera;
    providing a sensor array that takes an image by capturing the light from the illumination system reflected from the field of view;
    providing an image processor that processes the images from the sensor array for storage or transmission; and
    providing a clock generation circuit that provides one or more clock signals to operate the image processor; and
    controlling a frequency of operation of the clock signals in response to a control signal derived from an output signal of a sensor, wherein the output signal is provided from a secondary sensor which comprises a semiconductor-based thermometer that includes a transistor thermometer based on thermal characteristics of at least one P-channel transistor or at least one N-channel transistor.

8. A method as in claim 7, wherein the at least one P-channel transistor or the at least one N-channel transistor is long channel.

* * * * *